United States Patent
Zhang et al.

(10) Patent No.: US 11,744,913 B2
(45) Date of Patent: Sep. 5, 2023

(54) FLUID CONDUIT DISINFECTOR

(71) Applicant: BOLB INC., San Jose, CA (US)

(72) Inventors: Jianping Zhang, San Jose, CA (US); Ling Zhou, San Jose, CA (US); Ying Gao, San Jose, CA (US); Huazhong Deng, San Jose, CA (US); Peter Gordon, San Jose, CA (US); Cuong Le, San Jose, CA (US)

(73) Assignee: BOLB INC., Livermore, CA (US)

( * ) Notice: Subject to any disclaimer, the term of this patent is extended or adjusted under 35 U.S.C. 154(b) by 0 days.

(21) Appl. No.: 17/090,778

(22) Filed: Nov. 5, 2020

(65) Prior Publication Data

US 2022/0133940 A1    May 5, 2022

(51) Int. Cl.
*A61L 9/20* (2006.01)
*B05B 15/50* (2018.01)
*B05B 1/18* (2006.01)

(52) U.S. Cl.
CPC .......... *A61L 9/20* (2013.01); *B05B 15/50* (2018.02); *A61L 2209/12* (2013.01); *A61L 2209/14* (2013.01); *B05B 1/18* (2013.01)

(58) Field of Classification Search
None
See application file for complete search history.

(56) References Cited

U.S. PATENT DOCUMENTS

| | | | | |
|---|---|---|---|---|
| 7,498,004 | B2 * | 3/2009 | Saccomanno | C02F 1/325 422/186 |
| 9,310,088 | B2 * | 4/2016 | Melikov | G16H 50/80 |
| 9,551,996 | B2 * | 1/2017 | Baumgartner | A61L 9/14 |
| 11,040,601 | B2 * | 6/2021 | Line | B60H 1/00742 |
| 2007/0253860 | A1 * | 11/2007 | Schroder | B01D 53/8675 422/4 |
| 2010/0096564 | A1 * | 4/2010 | Yang | B82Y 10/00 250/492.1 |
| 2015/0064069 | A1 * | 3/2015 | Yi | A61L 9/20 422/121 |
| 2019/0142986 | A1 * | 5/2019 | Zhang | A61L 2/10 250/436 |
| 2019/0142987 | A1 * | 5/2019 | Zhang | C02F 1/32 250/435 |

FOREIGN PATENT DOCUMENTS

RO    118844 B    * 12/2003
RO    118844 B    * 12/2003

* cited by examiner

*Primary Examiner* — Andrew Smyth
(74) *Attorney, Agent, or Firm* — J.C. PATENTS

(57) ABSTRACT

A fluid conduit disinfector includes a conduit with a fluid disinfection channel defined by inner side surface of the conduit, wherein the inner side surface of the conduit is reflective with a germicidal ultraviolet (GUV) light reflectance R of 50%-99%; a GUV light source for emitting GUV light into the fluid disinfection channel; a fan for forcing a fluid to be disinfected to flow through the fluid disinfection channel, and a filter for filtering particles from the fluid. The fluid disinfection channel may include a first section, a second section and a third section, wherein the first section has a cylindrical shape with a first diameter, the third section has a cylindrical shape with a third diameter larger than the first diameter, the second section has a truncated conical shape and is positioned between the first section and the third section.

10 Claims, 22 Drawing Sheets

FLUID CONDUIT DISINFECTOR

TECHNICAL FIELD

The present disclosure relates to a fluid conduit disinfector using disinfection light, such as germicidal ultraviolet light, to disinfect fluid.

DESCRIPTION OF THE RELATED ART

More and more evidences reveal that airborne viruses are responsible for epidemic/pandemic outbreaks. While transmission mechanisms of the recent outbreak of Covid-19 are still under debate, a research team at the University of Florida succeeded in isolating live viruses from aerosols collected at a distance of 7 to 16 feet from patients hospitalized with Covid-19, according to a report published by New York Times in August 2020. Disinfecting air, especially for air in confined spaces such as indoors or in transport vehicles, is foreseen to be mandatory in future to eliminate pandemic outbreaks such as influenza and Covid-19. Air disinfection, unlike surface and water disinfection, has its own characteristics. Most vital one is that viable air disinfection technologies need to treat large air flow rate, for example, from 100 liter per minute (LPM) for vehicles, to 1000 LPM for small rooms, to 10,000 LPM and more for homes and public indoor spaces. Another characteristic of air disinfection is that for the same deactivation rate, air disinfection may need critical dose orders of magnitude lower than that required by surface and water disinfections. For example, a recent research paper from Columbia University revealed that a germicidal ultraviolet light (GUV) dose as low as 1.7 mJ/cm$^2$ achieved a 99.9% deactivation rate of airborne Human Coronavirus (HCov-229E), a safe subrogate for severe acute respiratory syndrome coronavirus 2 (SARS-CoV-2) that causes Covid-19 disease (see: M. Buonanno, D. Welch, I. Shuryak, and D. Brenner, Scientific Reports, 10 (10285), 2020). Other surface disinfection tests (including ours) of HCov-229E establish the critical GUV dose to be 16 mJ/cm$^2$ to achieve 99.99% deactivation rate, i.e., ~12 mJ/cm$^2$ to achieve 99.9% deactivation rate. The encouraging difference may come from the fact that airborne viruses unlike those on surfaces have no place to shield from GUV light.

In the past, GUV generated by mercury lamps has been used in hospitals for room air disinfection. The problem with mercury lamp is that it is not easy to produce high intensity GUV, as such, it is not efficient to treat air through air conduits, which is indispensable in air disinfection with human presence. As U.S. patent application Ser. No. 16/842,760 points out that a linear light source (such as a mercury lamp) and a pointing directional light source deliver dose to air, where light absorption coefficient is negligible, according to equations $$\bar{J} = \frac{P(R+r_0)}{2G}\ln\frac{R}{r_0} \text{ and } J = \frac{PL}{G},$$

respectively, where J, P, G, R, $r_0$, and L are GUV dose, GUV power, air flow rate, conduit radius, linear light source radius, and conduit length. It is noted that these equations neglect GUV air absorption coefficient (~10$^{-6}$ cm$^{-2}$) and GUV reflections in the inner wall of the conduit. As seen from these equations, for normal geometry of a conduit (R, $r_0$, and L), pointing directional light sources always deliver more GUV dose with the same GUV power and air flow rate.

A pointing directional GUV light source can be an assembly of deep UV light-emitting diodes (DUV LEDs), which are made of nitride compound semiconductors such as AlN and AlGaN. These DUV LEDs can give emissions in the UVC region, i.e., 200-280 nm, which are highly germicidal and virucidal.

The present disclosure discloses efficient GUV conduit disinfectors for fluids including air, taking into consideration of light reflections on the inner surface of the conduit.

SUMMARY

An aspect of the present disclosure provides a fluid conduit disinfector including:

a conduit with a fluid disinfection channel defined by inner side surface of the conduit, wherein the inner side surface of the conduit is reflective with a germicidal ultraviolet (GUV) light reflectance R of 50%-99%;

a GUV light source disposed within the fluid disinfection channel for emitting GUV light into the fluid disinfection channel along an axial direction of the fluid disinfection channel;

a fan for forcing a fluid to be disinfected to flow through the fluid disinfection channel, and a filter for filtering particles from the fluid.

Another aspect of the present disclosure provides a fluid conduit disinfector including:

a conduit with a fluid disinfection channel defined by inner side surface of the conduit, the fluid disinfection channel including a first section, a second section and a third section, wherein the first section has a cylindrical shape with a first diameter, the third section has a cylindrical shape with a third diameter larger than the first diameter, the second section has a truncated conical shape and is positioned between the first section and the third section;

a GUV light source disposed at an inlet end of the fluid disinfection channel and within the first section for emitting GUV light into the fluid disinfection channel along an axial direction of the fluid disinfection channel;

a reflector disposed at an outlet end of the fluid disinfection channel for reflecting the GUV light; and a showerhead disposed at the outlet end downstream of the reflector.

Another aspect of the present disclosure provides a fluid conduit disinfector including:

a main conduit with a fluid disinfection channel defined by an inner side surface and two inner end surfaces of the main conduit;

a first auxiliary conduit connected into a side wall of the main conduit at an inlet end of the fluid disinfection channel for introducing a fluid to be disinfected into the fluid disinfection channel;

a first GUV light source disposed in the first auxiliary conduit for emitting GUV light into the fluid disinfection channel;

a second auxiliary conduit connected into the side wall of the main conduit at an outlet end of the fluid disinfection channel for discharging the fluid from the fluid disinfection channel;

a second GUV light source disposed in the second auxiliary conduit for emitting GUV light into the fluid disinfection channel;

wherein a ratio of an area of the inner side surface that is occupied by the first and second auxiliary conduits to an entire area of the inner side surface and the two inner end surfaces is less than 0.1.

Another aspect of the present disclosure provides a fluid conduit disinfector including:

a main conduit with a fluid disinfection channel defined by an inner side surface and an inner end surface of the main conduit, the fluid disinfection channel including a first section, a second section and a third section, wherein the first section has a cylindrical shape with a first diameter, the third section has a cylindrical shape with a third diameter larger than the first diameter, the second section has a truncated conical shape and is positioned between the first section and the third section;

an auxiliary conduit connected into a side wall of the main conduit at an inlet end of the fluid disinfection channel for introducing a fluid to be disinfected into the fluid disinfection channel;

a GUV light source disposed in the auxiliary conduit for emitting GUV light into the fluid disinfection channel;

a reflector disposed at an outlet end of the fluid disinfection channel for reflecting the GUV light; and a showerhead disposed at the outlet end downstream of the reflector.

Another aspect of the present disclosure provides a fluid conduit disinfector including:

two or more disinfection units connected in series in fluid communication, wherein each disinfection unit has two fluid disinfection channels arranged side-by-side and separated from each other with a separation wall, the two fluid disinfection channels are merged at one end, a GUV light source is disposed within each of the two fluid disinfection channels at the other end, respectively, for emitting GUV light into corresponding fluid disinfection channel, each of the two fluid disinfection channels has a sloped inner surface at the merged end for reflecting the GUV light from one disinfection channel towards the other disinfection channel, wherein the two or more disinfection units are arranged side-by-side and separated by separation walls.

Another aspect of the present disclosure provides a fluid conduit disinfector including:

a conduit defining a fluid disinfection channel, wherein the inner surface of the fluid disinfection channel is reflective with a germicidal ultraviolet (GUV) light reflectance R of 50%-99%, the fluid disinfection channel has a lateral dimension D and a length L;

a fluid inlet for introducing a fluid to be disinfected into the fluid disinfection channel, wherein the fluid inlet has a lateral dimension d;

a GUV light source disposed within the fluid inlet for emitting GUV light into the fluid disinfection channel;

a fan disposed within the fluid inlet;

a filter disposed within the fluid inlet; and a reflector disposed within the fluid disinfection channel and in front an outlet;

wherein $$\frac{D}{d} \geq 5, \text{ and } \frac{D}{L} \geq 3.$$

BRIEF DESCRIPTION OF THE DRAWINGS

The accompanying drawings, which are included to provide a further understanding of the disclosure and constitute a part of this application, illustrate embodiments of the invention and together with the description serve to explain the principle of the disclosure. Like reference numbers in the figures refer to like elements throughout, and a layer can refer to a group of layers associated with the same function.

DETAILED DESCRIPTION OF EMBODIMENTS

In the following description, for the purposes of explanation, specific details are set forth in order to provide an understanding of the disclosure. It will be apparent, however, to one skilled in the art that the disclosure can be practiced without these details. One skilled in the art will recognize that embodiments of the present disclosure, described below, may be performed in a variety of ways and using a variety of means. Those skilled in the art will also recognize additional modifications, applications, and embodiments are within the scope thereof, as are additional fields in which the disclosure may provide utility. Accordingly, the embodiments described below are illustrative of specific embodiments of the disclosure and are meant to avoid obscuring the disclosure.

Figure 1:
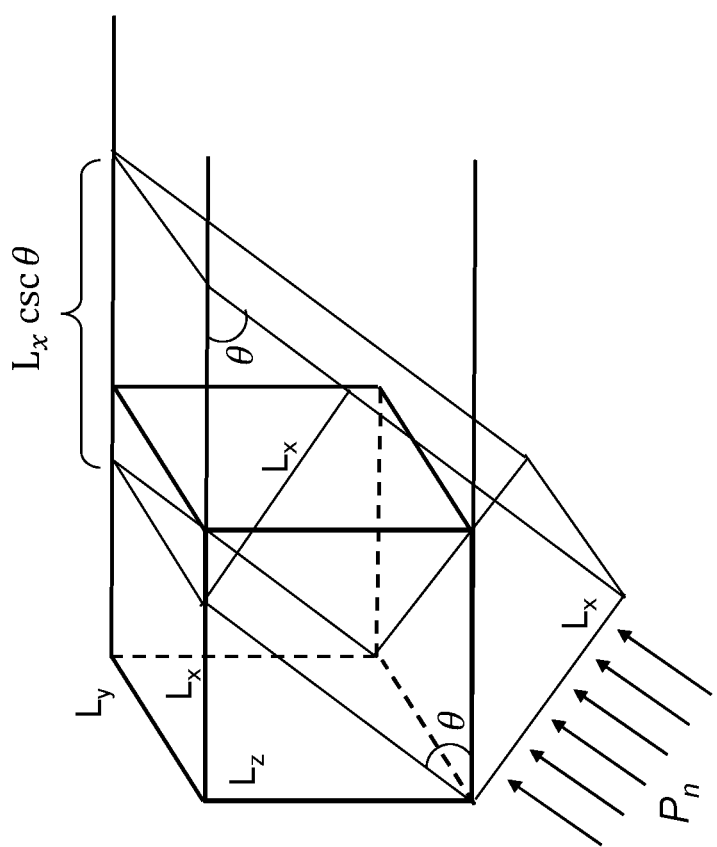
FIG. 1 illustrates a model to compare the dose delivery efficiencies of parallel, perpendicular, and slanted-beam dose delivery schemes.

FIG. 1 Illustrates a model to compare the dose delivery efficiencies of parallel, perpendicular, and slanted-beam dose delivery schemes. In the parallel dose delivery scheme, light beams are in parallel with fluid flow, so that the delivered dose $J_\parallel$ is:

$$J_\parallel = \frac{P_0}{\alpha G}(1 - e^{-\alpha L_x}) \quad \text{(Eq. 1)}$$

Where $P_0$, $\alpha$, $G$ and $L_x$ are impinge light power, fluid's light absorption coefficient, volumetric flow rate, and parallel light path length, respectively. As seen, if $L_x$ is substantially large, or more precisely, if $\alpha L_x$ is substantially large, $J_\parallel$ approaches $J_{\parallel\infty}$, which is, $$J_{\parallel\infty} = \frac{P_0}{\alpha G} \quad \text{(Eq. 2)}$$

In this specification, Eq. 2 is called parallel beam limit. It calculates the maximum dose allowed by the parallel dose delivery scheme.

According to one aspect of the present disclosure, $\alpha L_x \geq 4.6$, hence $J_\parallel \geq 0.99 J_{\parallel\infty}$, is considered substantially large in this specification.

In the perpendicular dose delivery scheme, light beams are perpendicular to fluid flow. Suppose the perpendicular channel height is $L_z$, with reflectance R to sustain unlimited reflections, so the delivered dose $J_{\perp\infty}$ is:

$$J_{\perp\infty} = \frac{P_0}{\alpha G} \frac{1 - e^{-\alpha L_z}}{1 - R e^{-\alpha L_z}} \quad \text{(Eq. 3)}$$

Figure 2:
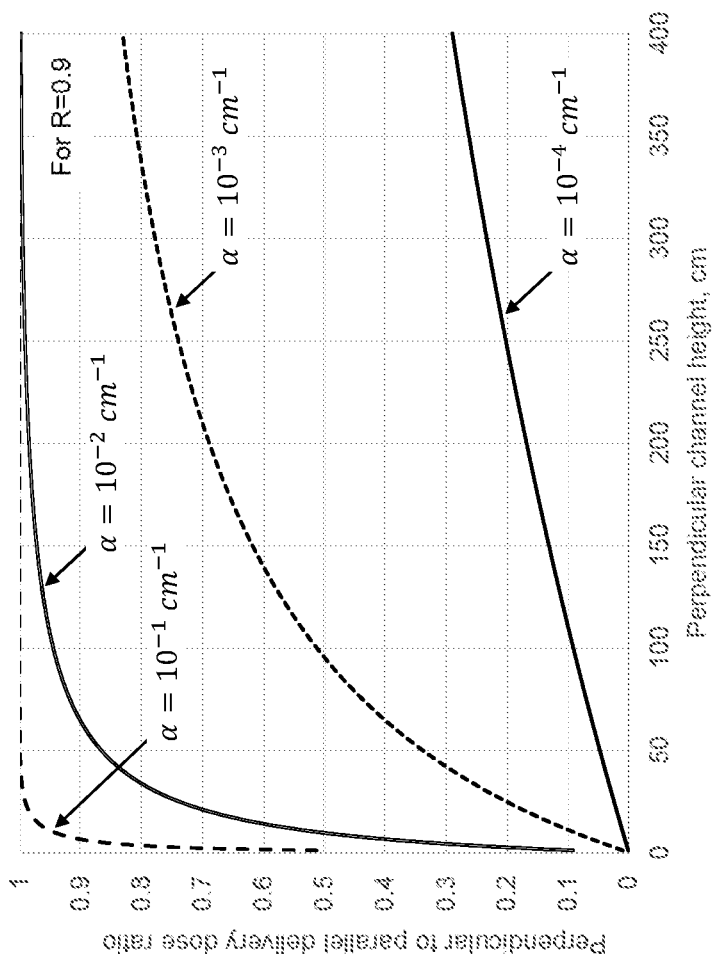
FIG. 2 plots dose delivery ratios of perpendicular and parallel dose delivery schemes according to one aspect of the present disclosure.
Figure 3:
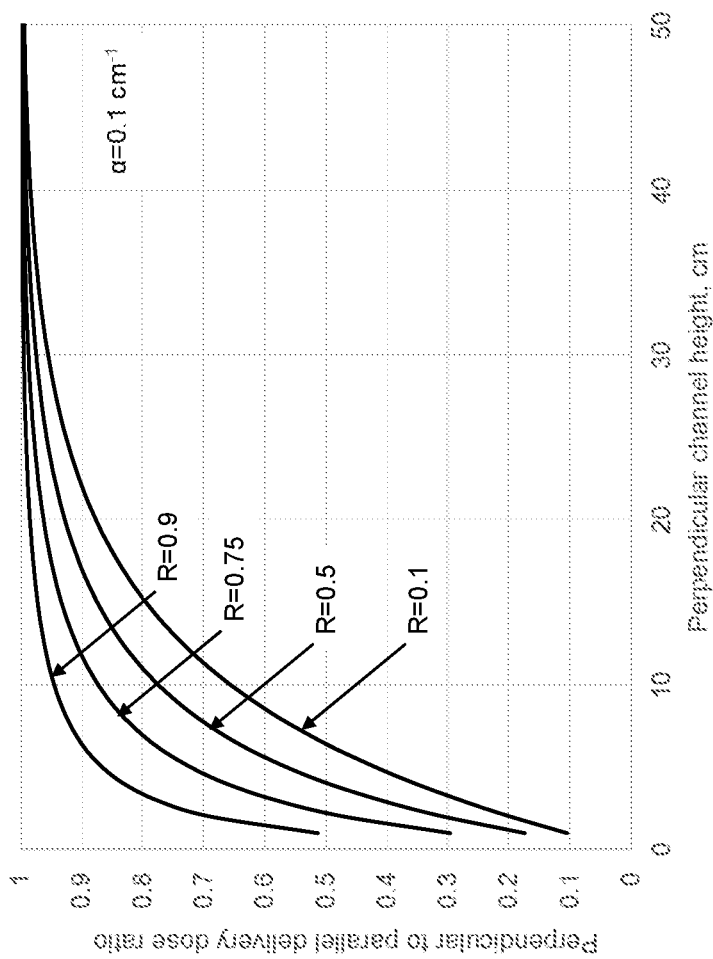
FIG. 3 plots the effect of reflectance on dose delivery efficiency ratios of perpendicular and parallel dose delivery schemes for highly absorptive fluid.

Dividing Eq. 3 by Eq. 2, one obtains the dose delivery efficiency ratio of the ideal perpendicular to parallel dose delivery schemes, i.e., $$\frac{J_{\perp\infty}}{J_{\parallel\infty}} = \frac{1 - e^{-\alpha L_z}}{1 - R e^{-\alpha L_z}} \quad \text{(Eq. 4)}$$

$$\frac{J_{\perp\infty}}{J_{\parallel\infty}} \leq 1 \text{ as } R \leq 1,$$

meaning perpendicular dose delivery scheme is always less efficient than parallel dose delivery scheme. To graphically demonstrate this, R is set to be 0.9, and the dose delivery ratios $$\left(\frac{J_{\perp\infty}}{J_{\parallel\infty}}\right)$$

are compared in FIG. 2, tor a set of different light absorption coefficients $\alpha$'s. Therefore, according to one aspect of the present disclosure, for small $\alpha$'s ($\alpha \leq 10^{-2}$ cm$^{-1}$, which is true for air and clean water disinfections) within reasonable perpendicular channel height, perpendicular dose delivery scheme is inferior in dose delivery efficiency to parallel dose delivery scheme. For large $\alpha$'s ($\alpha > 10^{-2}$ cm$^{-1}$, which is true for milk and fruit juice disinfections) because of strong fluid UV absorption, the doses delivered converge for the perpendicular and parallel dose delivery schemes within reasonable perpendicular channel height. When disinfecting highly UV absorptive fluids like fruit juices and milk, it is shown in FIG. 3 that improving the reflectance can reduce perpendicular channel height for the perpendicular dose delivery scheme to compete with the parallel dose delivery scheme.

More general, consider a slanted-beam dose delivery scenario, where light is shone in a slanted angle, say with impinge angle $\theta$ to the fluid flow direction, as shown in FIG. 1. In this specification, impinge angle $\theta$ is defined as the angle between a light ray and its receiving surface. For simplicity, suppose the model shown in FIG. 1 is a square conduit, with cross-section area $L_y \times L_z = D^2$ and fluid with GUV light absorption coefficient $\alpha$ flowing in the x-direction with volumetric flow rate G. Consider this is the event between n-th and (n+1)-th reflection. After n-th reflection, the impinge power becomes $P_n = P_0 R^n e^{-\alpha n D \csc \theta}$. Consider $P_n$ has a vertical component $P_n \sin \theta$ and a horizontal component $P_n \cos \theta$ impinging perpendicular and parallel to fluid flow G within the square conduit, respectively. The horizontal component power $P_n \cos \theta$ impinges perpendicularly on a cross-section area of $D^2$, and the vertical component $P_n \sin \theta$ impinges perpendicularly on an area of $D^2 \csc \theta$, as illustrated in FIG. 1. Between n-th and (n+1)-th reflections, the fluid flow's exposure time to GUV is $$t_n = \frac{D^3 \csc \theta}{G},$$

hence the horizontal and the vertical power components deliver $$\text{doses } J_{n1} = \frac{P_n \cos \theta}{\alpha G}(1 - e^{-\alpha D \csc \theta}) \text{ and } J_{n2} = \frac{P_n \sin \theta}{\alpha G}(1 - e^{-\alpha D})$$

to fluid flow between n-th and (n+1)-th reflections, respectively. Summing up $J_{n1}$ and $J_{n2}$ for all reflections leads to the following equation (Eq. 5).

$$J = \frac{P_0}{\alpha G}(\cos\theta - \cos\theta e^{-\alpha D\csc\theta} + \sin\theta - \sin\theta e^{-\alpha D})\frac{1 - R^{n+1}e^{-\alpha(n+1)D\csc\theta}}{1 - Re^{-\alpha D\csc\theta}} \quad \text{(Eq. 5)}$$

When $\theta \to 0$ and $\alpha > 0$, Eq. 5 coincides with parallel beam limit, i.e. Eq. 2.

The parallel beam limit can deliver very large dose as $\alpha$ vanishes (like in air: $\alpha \sim 10^{-6}$ cm$^{-1}$).

When $n \to \infty$, and $\theta > 0$, i.e., for unlimited reflections, Eq. 5 becomes, $$J = \frac{P_0}{\alpha G}(\cos\theta - \cos\theta e^{-\alpha D\csc\theta} + \sin\theta - \sin\theta e^{-\alpha D})\frac{1}{1 - Re^{-\alpha D\csc\theta}} \quad \text{(Eq. 6)}$$

When $\theta \to 90°$, Eq. 6 converges with Eq. 3.
When $\alpha \to 0$, and $\theta > 0$, Eq. 5 reduces to, $$J = \frac{P_0 D}{G}(\sin\theta + \cot\theta)\frac{1 - R^{n+1}}{1 - R} \quad \text{(Eq. 7)}$$

When $n \to \infty$, Eq. 7 becomes, $$J = \frac{P_0 D}{G}(\sin\theta + \cot\theta)\frac{1}{1 - R} \quad \text{(Eq. 8)}$$

Figure 11:
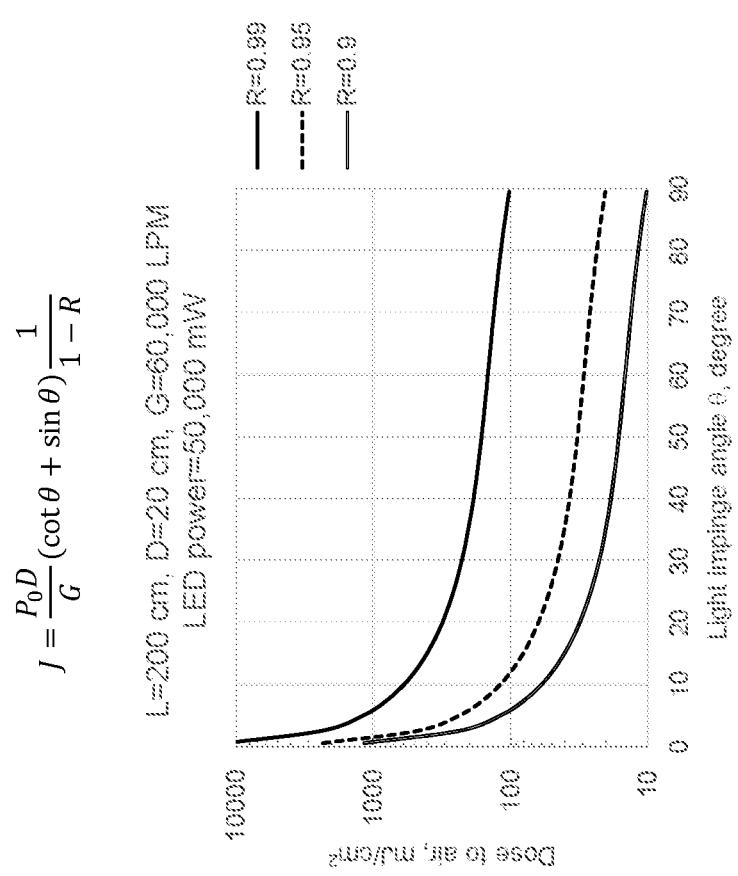
FIG. 11 plots doses as function of light impinge angles for three different reflectance of a conduit disinfector according to an embodiment of the present disclosure.
Figure 12:
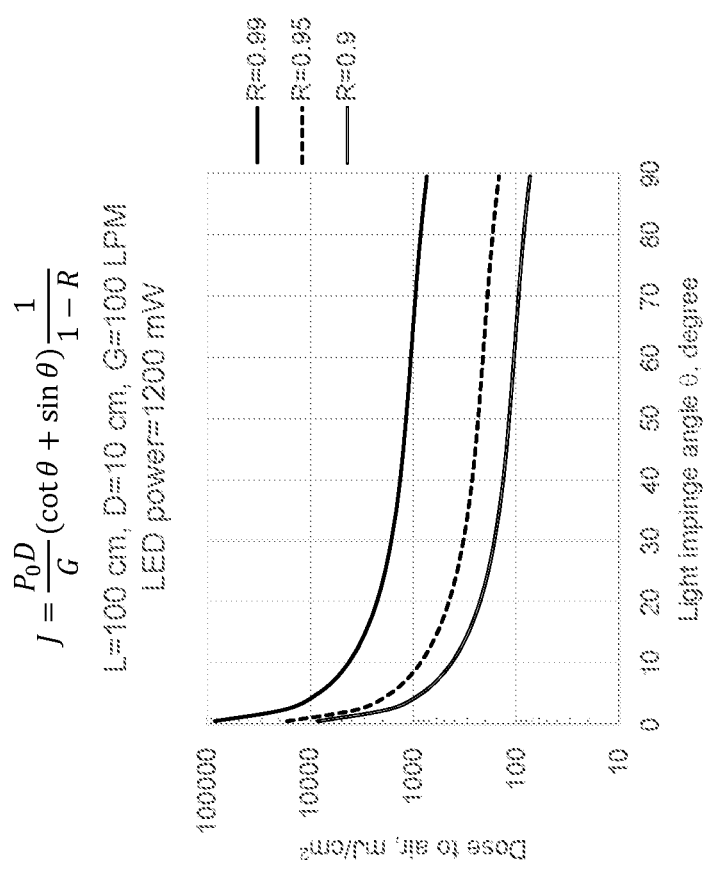
FIG. 12 plots doses as function of light impinge angles for three different reflectance of a conduit disinfector according to an embodiment of the present disclosure.

Eqs. 5 and 6 are general and apply to fluid disinfection of all kinds with non-negligible absorption coefficient, while Eqs. 7 and 8 can be useful for GUV air disinfector designs where absorption coefficient is negligible. Further, notice that Eqs. 7 and 8 are monotonically decreasing functions of impinge angle $\theta$ for $\theta \in (0, \frac{\pi}{2}]$ (also visualized in FIGS. 11 and 12).

Comparing Eqs. 7 and 8, if an air conduit disinfector is not designed to hold for unlimited reflections, the air conduit disinfector may have a design efficiency, $\rho$, less than 1, defined by the division of Eq. 7 over Eq. 8, i.e., $$\rho = 1 - R^{n+1} \quad \text{(Eq. 9), and,}$$

$$n(\rho, R) = \log_R(1-\rho) - 1 \quad \text{(Eq. 10)}$$

Where $n(\rho, R)$ is the minimal reflection times required to have design efficiency $\rho$ for an air conduit disinfector of reflectance R.

Figure 4:
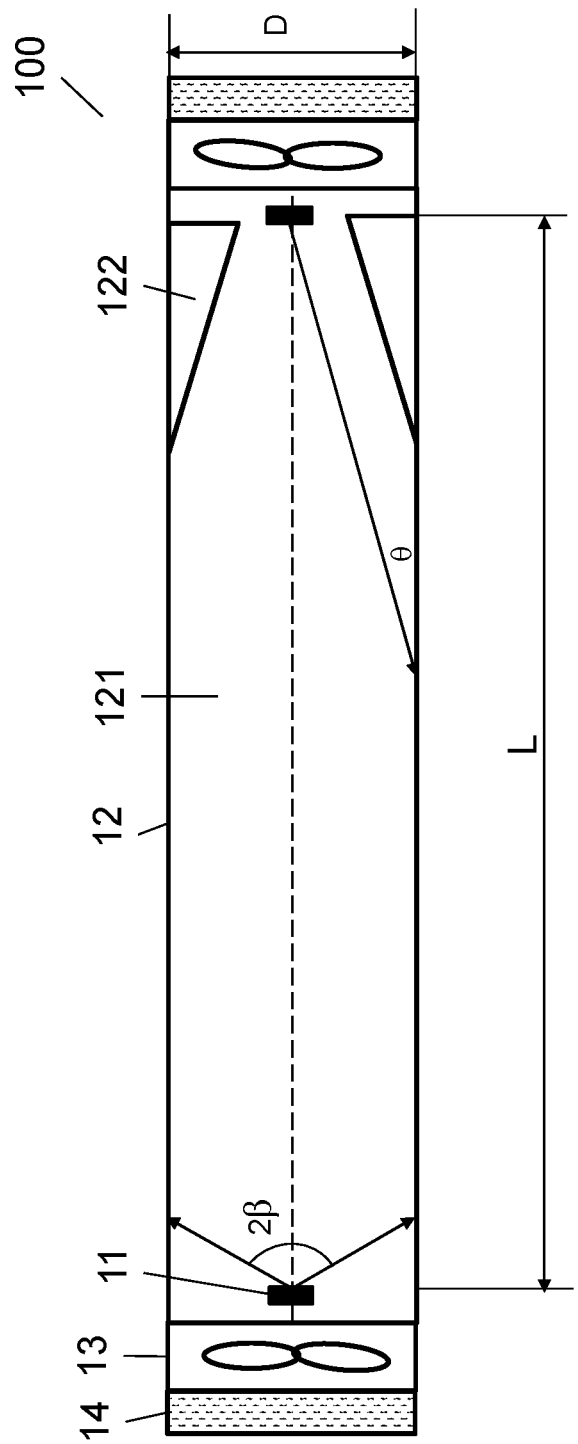
FIG. 4 illustrates a cross-sectional schematic view of a fluid conduit disinfector according to an embodiment of the present disclosure.
Figure 9:
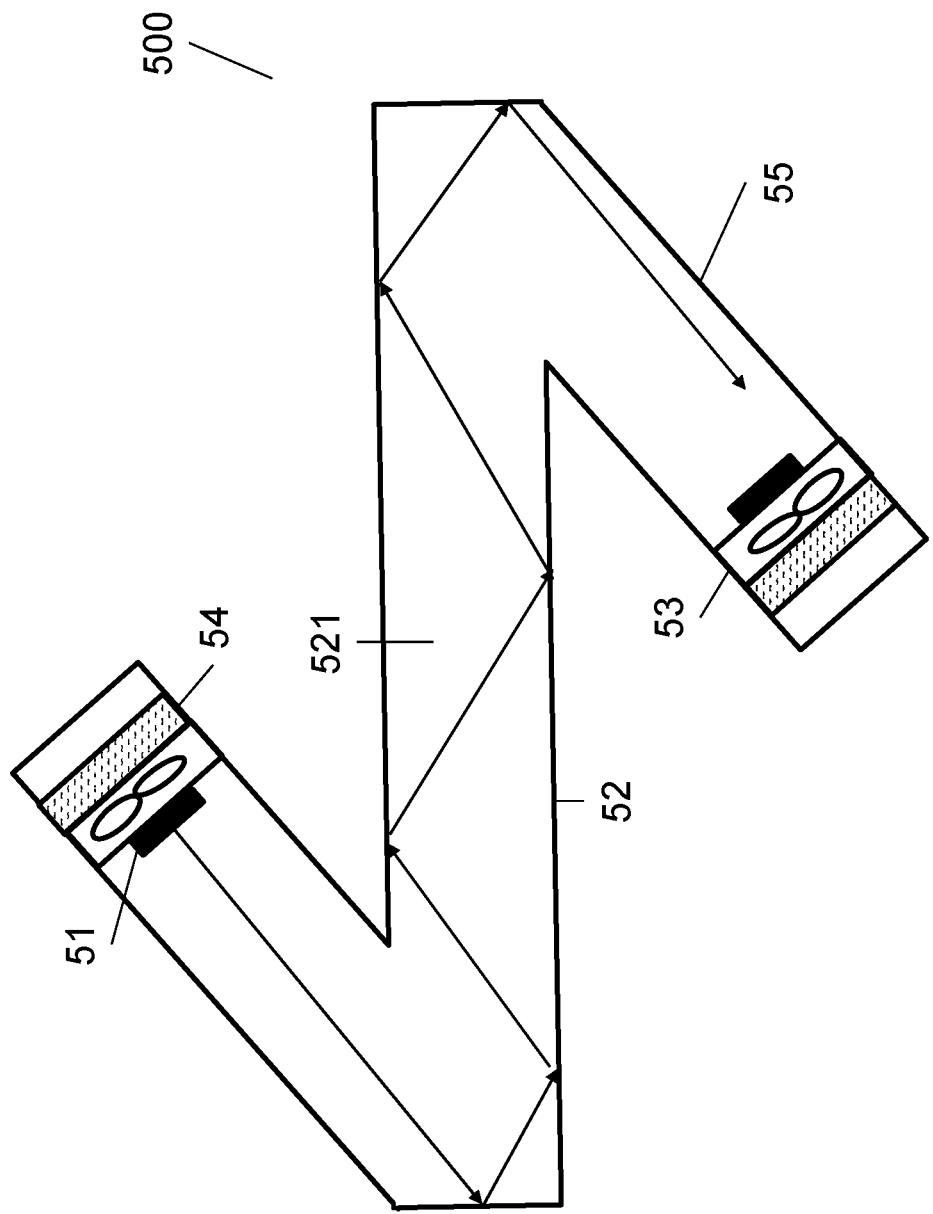
FIG. 9 illustrates a cross-sectional schematic view of a fluid conduit disinfector according to an embodiment of the present disclosure.

Illustrated in FIG. 4 is a cross-sectional schematic view of a fluid conduit disinfector 100 (or air conduit disinfector 100) according to one aspect of the present disclosure, including a GUV light source 11 and a conduit 12. It may also include supplementary elements such as fans 13 for sucking in/blowing out air, particle filters 14 for maintaining cleanness of the inner surfaces of conduit 12, and reflector 122 surrounding the GUV light source 11 for focusing light beams of GUV light source 11. Conduit 12 housing a fluid disinfection channel 121 of length L and lateral dimension (cross-section width, or diameter) D can be a circular tube, a rectangular or square tube, or other suitable type of conduit. Fluid disinfection channel 121 as shown in FIG. 4 is a straight channel, it also can be of other shape, such as a Z shape as shown in FIG. 9. Light source 11 is placed within fluid disinfection channel 121, optionally on its axis and at the end of conduit 12. There may be a light source 11 at each end of fluid disinfection channel 121 or conduit 12, and it can be DUV LEDs, or any other suitable GUV light sources. Light source 11 emits GUV light with angles, $\theta$, defined as impinge angles in this specification, to the inner surface of conduit 12, as shown in FIGS. 1 and 4. The inner surface of conduit 12 is reflective, with reflectance R. For example, the inner surface can be polished aluminum or coated with aluminum thin film with GUV reflectance of 90%, or can be coated with teflon with DUV reflectance of 95%, or can be coated with microporous teflon with reflectance of 98-99%. The reflections can be diffusive or specular, even though specular reflections are illustrated in FIG. 1 for clarity and simplicity.

In the embodiment according to FIG. 4, as the two ends of conduit 12 may be non-reflective for having filters 14 and fans 13 for air circulation, the reflection times, n, is therefore limited by $$\frac{L}{D \cot\theta},$$

i.e., $$n(L, D, \theta) = \frac{L}{D \cot\theta} \quad \text{(Eq. 11)}$$

According to Eqs. 10 and 11, therefore the design of conduit 12, i.e., the selection of L, D, and $\theta$ has to satisfy Eq. 12.

$$\theta \geq \tan^{-1}\frac{D}{L}[\log_R(1-\rho) - 1] \quad \text{(Eq. 12)}$$

This tells that to obtain a target design efficiency, $\rho$, with a set of given disinfection channel parameters (i.e., channel length L, lateral dimension D, and reflectance R), light impinge angle $\theta$ has to be no less than a critical value as defined by inequality Eq. 12.

When GUV light source 11 emits light of parallel beams, such as being a GUV laser or GUV LED of very narrow beam dispersion angle (such as less than 20°), it is easy to manipulate the impinge angle $\theta$ (such as tilting the light source to an angle $\theta$ with respect to the light receiving surface) to satisfy Eq. 12.

More practically, GUV light source 11 may emit light with many impinge angles, i.e., it may deliver optical power in a cone or frustum shape, with a cone angle $2\beta$. For a GUV light source 11 of light cone angle $2\beta$ situated at the axis of disinfection channel 121 and emitting along the axis, as illustrated in FIG. 4, one aspect of the present disclosure requires $\beta$ to satisfy eq. 13:

$$\beta \geq \theta \geq \tan^{-1}\frac{D}{L}[\log_R(1-\theta) - 1] \quad \text{(Eq. 13)}$$

Here 2β is the cone angle of a light cone consisting at least 50% of the total emitted optical power. The cone angle or aperture of a right circular cone is the maximum angle between two generatrix lines: i.e., if the generatrix makes an angle β to the axis, the aperture is 2β. When GUV light source 11 is made of DUV LEDs, lens attached to DUV LEDs can modify light cone angles. For example, a hemisphere lens usually results in large cone angle of 120°-150°. Aspheric lens can focus light beam to much small cone angle of 30°-40°. Reflectors (such as reflector 122 shown in FIG. 4) being parabolic or spheric can further modify light cone angle.

Figure 5:
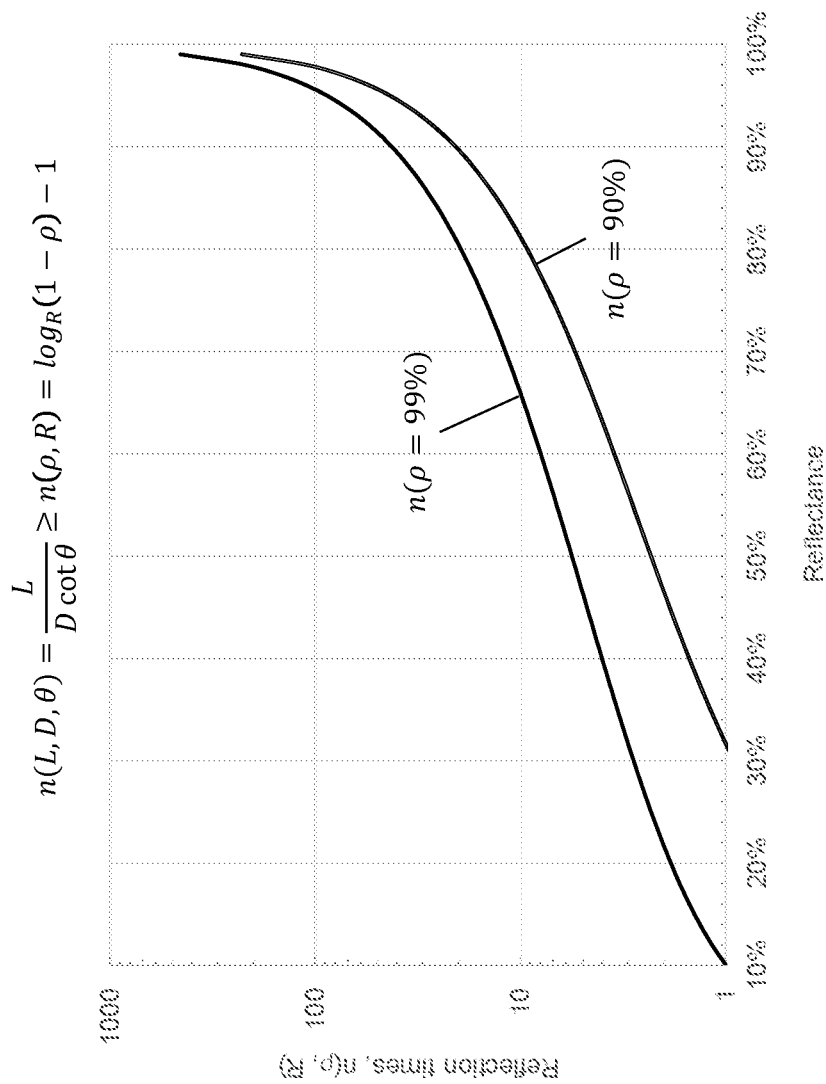
FIG. 5 plots the minimal reflections needed as function of reflectance for given design efficiencies of 90% and 99% of the embodiment shown in FIG. 4.

This selection rule is graphically revealed in FIG. 5, where the minimal reflections needed are plotted as function of reflectance for given design efficiencies of 90% and 99%. By selecting disinfection channel length L, lateral dimension (cross-section width or diameter) D and light impinge angle θ, conduit 12 according one aspect of the present disclosure has to accommodate light reflection times not less than $\log_R(1-\rho)-1$, for any given design efficiency ρ and inner surface reflectance R. For example, if the conduit inner surface having reflectance R of 90% and the required design efficiency ρ being 90%, therefore the selection of L, D, and θ has to satisfy $$\frac{L}{D \cot \theta} \geq 21.$$

If R=60% and ρ=99%, then the selection of L, D, and θ has to satisfy $$\frac{L}{D \cot \theta} \geq 8,$$

etcetera.

On the other hand, another air disinfector embodiment made according to fluid conduit disinfector 100 may hold unlimited light reflections, by using GUV reflective filters 14 and fans 13. For example, the surface of filters 14 and fans 13 can be coated with GUV reflective materials, e.g., coated with aluminum thin film with GUV reflectance of 90%, or coated with teflon with DUV reflectance of 95%, or coated with microporous teflon with reflectance of 98-99%. Therefore, the selection of L, D, and θ does not have to satisfy Eqs. 12 and 13. The dose calculation in such an unlimited-light-reflection disinfector 100 follows Eqs. 6 or 8.

Figure 6:
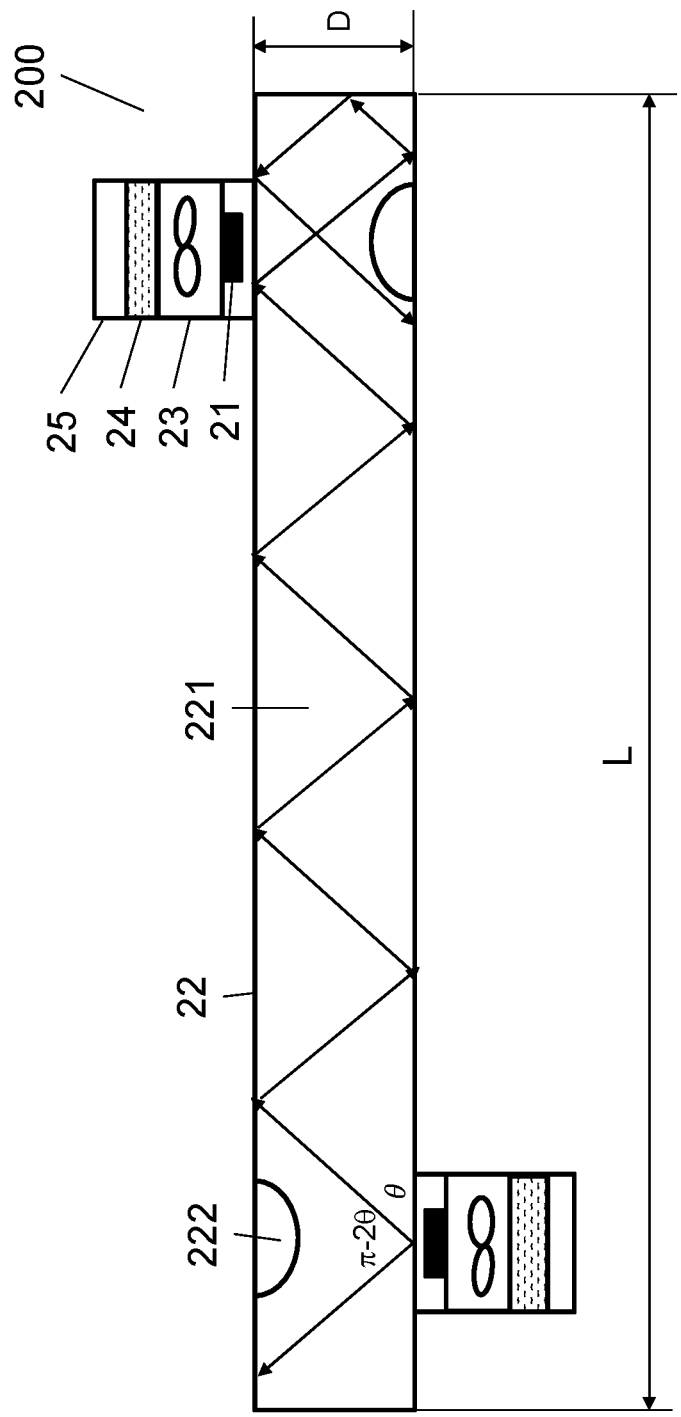
FIG. 6 illustrates a cross-sectional schematic view of a fluid conduit disinfector according to an embodiment of the present disclosure.

According to another aspect of the present disclosure, a fluid conduit disinfector 200 is provided with a cross-sectional schematic view illustrated in FIG. 6, capable of housing unlimited light reflections. Since the two reflective ends of conduit 22 is critical to sustain continuous reflections, GUV light source 21, fan 23 and filter 24 are retrieved away from the fluid disinfection channel 221, so that light can bounce back and forth within the disinfection channel 221 continuously. GUV light source 21, fan 23 and filter 24 are assembled in another conduit 25, which joins conduit 22 in a slanted angle or perpendicularly, allowing fluid to be introduced into and retracted from conduit 22. Defining f to be the ratio of the intersection areas (the areas of the inner surface of conduit 22 occupied by conduits 25) of conduits 25 (two of them shown in FIG. 6) to the whole inner surface area of conduit 22, the present disclosure requires f to be less than 10%, for example, to be 1-5%. This arrangement allows light to sustain unlimited reflections within disinfection channel 221 with minimal loss due to absorption on the intersection areas. The intersection area may reduce the effective reflectance of the inner surface of conduit 22 from R to (1−f)R. Optionally, GUV light source 21 in the embodiment shown in FIG. 6 emits GUV light upwardly or downwardly (relative to a horizontal fluid disinfection channel 221 as shown in FIG. 6), delivering a light cone with a large cone angle (or called as divergence angle, or aperture angle in this specification). This translates into small impinge angles θ to the inner surface of conduit 22. The cone angle of GUV light source 21 in FIG. 6 can be defined as π-2θ. According to one aspect of the present disclosure, for conduit disinfector 200, the impinge angle θ is preferably in the range of 0°-30°. Therefore, the cone angle of GUV light source 21 is in the range of 120°-180°. GUV light source 21 may be made of DUV LEDs, such as a DUV LED, or an array of DUV LEDs. To further reduce impinge angle θ, a convex reflector (mirror) 222 can be placed on the inner surface of conduit 22, facing directly to GUV light source 21 across the disinfection channel 221. The convex reflector 222 can be of parabolic, spherical, or aspheric shape with a diameter larger than the diameter of GUV light source 21, but smaller than the diameter of conduit 25. The convex reflector 222 can be made from the same material as the inner surface of conduit 12 as described previously.

Figure 7:
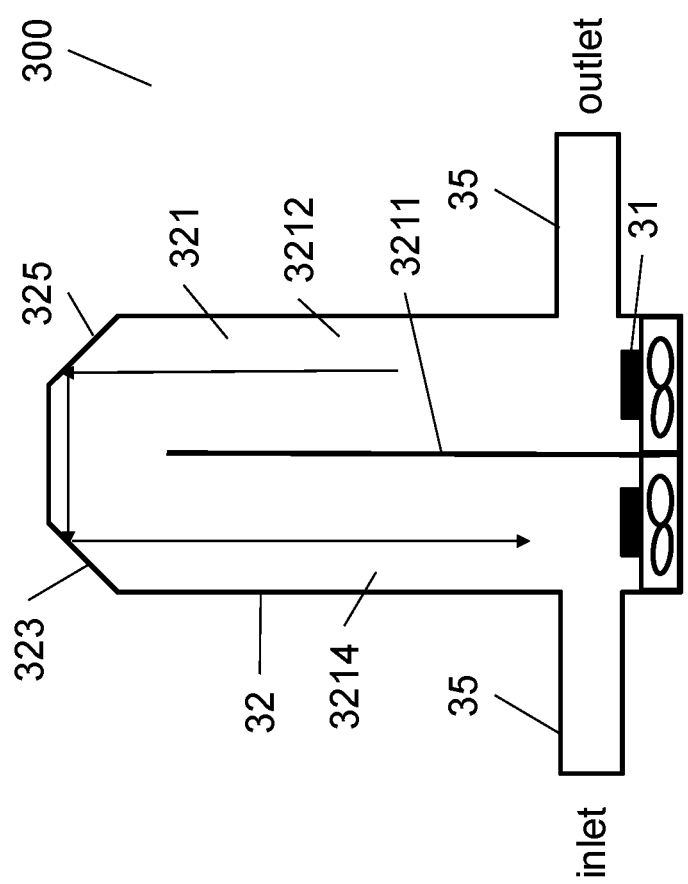
FIG. 7 illustrates a cross-sectional schematic view of a fluid conduit disinfector according to an embodiment of the present disclosure.
Figure 18:
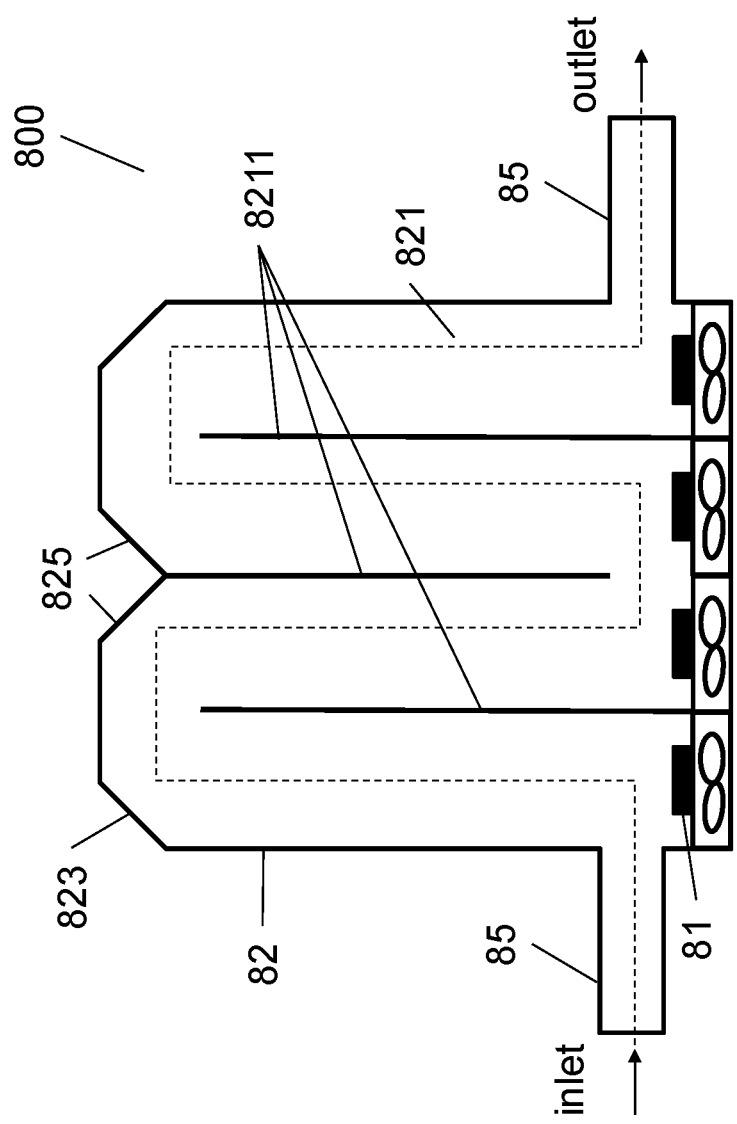
FIG. 18 illustrates a cross-sectional schematic view of a fluid conduit disinfector according to an embodiment of the present disclosure.

According to another aspect of the present disclosure, a fluid conduit disinfector 300 is provided, with a cross-sectional schematic view illustrated in FIG. 7. Two GUV light sources 31 (optionally with its own active cooling system such as cooling fan) are placed at the bottom of disinfection channel 321. Fluid flows in and out of disinfection channel 321 through side conduits 35. And disinfection channel 321 has a separation wall 3211 dividing the disinfection channel into left and right two channels (3212, 3214), doubling fluid disinfection channel length. Conduit 32 housing disinfection channel 321 has two slope ceilings 323 and 325 for reflecting GUV light, allowing light exchange between disinfection channels 3212 and 3214. The inner surfaces of disinfection channels 3212 and 3214 are reflective to GUV light and can be made from the same material as the inner surface of conduit 12 as described previously. Connecting two or more conduit disinfectors 300 in series can form a new conduit disinfector 800, as illustrated in FIG. 18.

Figure 8:
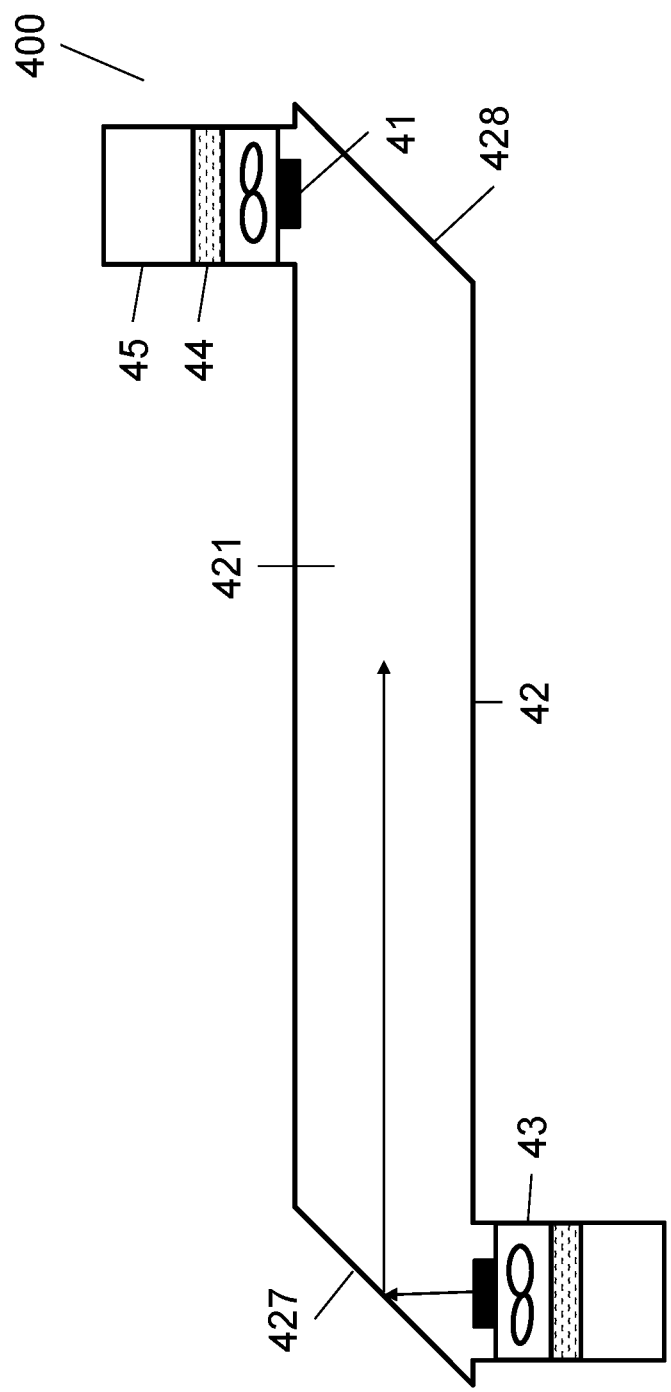
FIG. 8 illustrates a cross-sectional schematic view of a fluid conduit disinfector according to an embodiment of the present disclosure.

According to yet another aspect of the present disclosure, a fluid conduit disinfector 400 is provided, with a cross-sectional schematic view illustrated in FIG. 8. GUV light source 41, fan 43 and filter 44 are retrieved away from the fluid disinfection channel 421, so that light can bounce back and forth within the fluid disinfection channel 421 continuously. GUV light source 41, fan 43 and filter 44 are assembled in another conduit 45, which joins conduit 42 in a slanted angle or perpendicularly, allowing fluid to be introduced into and retracted from conduit 42. The structure of fluid conduit disinfector 400 is similar to fluid conduit disinfector 200. Major difference is that the two ends of conduit 42, i.e., inner end surfaces 427 and 428 are tilted and facing the GUV light source 41, respectively. For example, inner end surfaces 427 and 428 can be a planar plane and tilted at 45° angle to the axis of fluid disinfection channel 421 and can be made from the same material as the inner surface of conduit 12 as described previously.

According to still another aspect of the present disclosure, a fluid conduit disinfector 500 is provided, with a cross-sectional schematic view illustrated in FIG. 9. GUV light source 51, fan 53 and filter 54 are disposed in the conduit 55 (two conduits 55 are shown in FIG. 9), which joins conduit 52 in a slanted angle, for example between 20-50°, in a symmetrical manner with two inner end surfaces of conduit 52 being perpendicular to the axis of conduit 52. Conduits 52 and 55 jointly housing a fluid disinfection channel 521. Light and fluid travel in fluid disinfection channel 521 in a "Z-shaped" path, allowing for more dose delivery. All the inner surface of fluid disinfection channel 521 are reflective to GUV light and can be made from the same material as the inner surface of conduit 12 as described previously.

EXAMPLES

Figure 10:
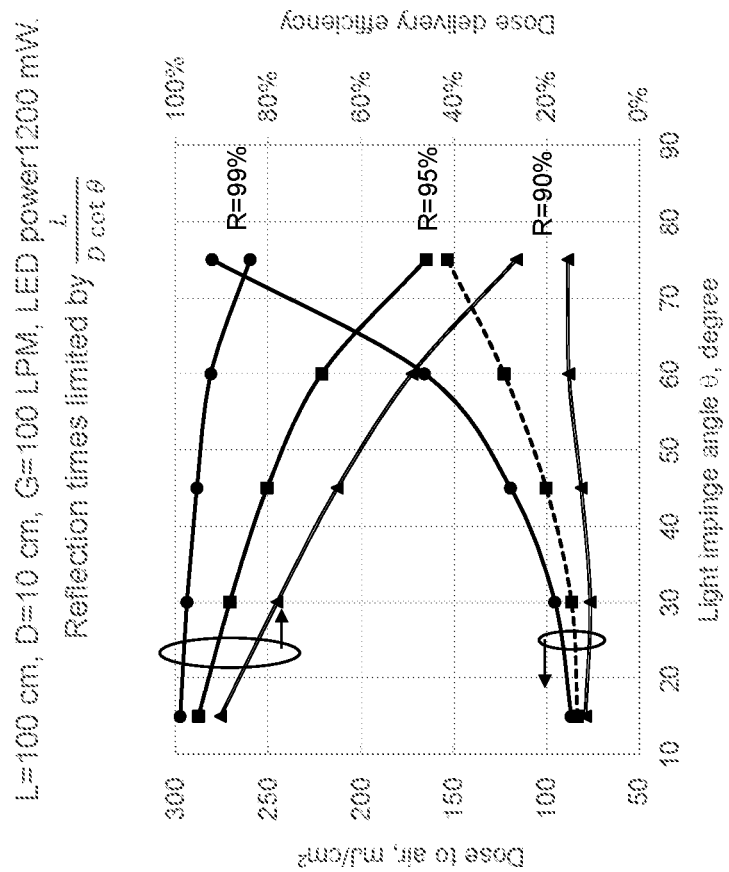
FIG. 10 plots doses and dose delivery efficiencies as function of light impinge angles for three different reflectance of a conduit disinfector according to an embodiment of the present disclosure.

As an example, a cylindrical air conduit disinfector, made according to conduit disinfector 100, has a fluid disinfection channel length L=100 cm, diameter D=10 cm. As the two ends of fluid disinfection channel 121 are non-reflective (due to filters and fans in conduit disinfector 100), here the design efficiency p is different for different impinge angles. Taking air flow rate G=100 LPM and GUV light power to be 1200 mW, FIG. 10 plots (following Eq. 7) doses and dose delivery efficiencies as function of light impinge angles for three different reflectance of a conduit disinfector made according to FIG. 4. Overall, the higher the reflectance, the more the dose delivered. Notice that as the disinfection length is fixed (100 cm) and the two ends are not reflective, the smaller the impinge angle is, the less times the reflection occurs (Eq. 11), resulting in the smaller the doses delivered. To mitigate this problem, one way is to increase light impinge angles, as FIG. 10 suggests. Another way is to enlarge the disinfection channel length allowing for more reflections for smaller impinge angles, according to Eqs. 11 and 12. Further, notice that for this fixed design, if a practical reflectance R=90% and impinge angle θ=75° are chosen, the device can deliver about 88 mJ/cm$^2$ to 100 LPM air flow. If the GUV dose to deactivate 99.9% of SARS-Cov-2 viruses is 1.7 mJ/cm$^2$, this conduit disinfector can disinfection air flow of 5,000 LPM. The dose delivery efficiency plotted in FIG. 10 reflects light loss due to multiple reflections. Smaller impinge angles show higher dose delivery efficiency because they allow for less reflection times hence less loss due to reflection. If reflection times are not limited, smaller impinge angles will deliver more dose. Generally, depending on the fluid flow rate, the length L and diameter D of the fluid disinfection channel 121 can be in the range of 10-500 cm and 5-100 cm, respectively, and preferably satisfy Eq. 13 if filters 14 and fans 13 are GUV non-reflective. Depending on dosage required, in general, the air flow rate G can be in the range of 50-10,000 LPM and GUV light power can be in the range of 500-3000 mW.

Another cylindrical air conduit disinfector, made according to fluid conduit disinfector 200 to harvest the unlimited reflections, has a fluid disinfection channel length L=200 cm, diameter D=20 cm. The treated air flow rate is G=60,000 LPM for residential home purpose, and GUV light power is 50 W. The doses delivered to the air flow with different impinge angles are plotted in FIG. 11 (following Eq. 8). Again, the higher the reflectance, the more the dose. Here, since the reflection times are unlimited, clearly the smaller the impinge angle, the larger the dose delivered. According to one aspect of the present disclosure, for fluid conduit disinfector 200, the impinge angle θ is preferably in the range of 0°-30°. Selecting practical reflectance R=90% and impinge angle θ=15°, this device delivers about 40 mJ/cm$^2$ to 60,000 LPM air flow.

Still another air disinfector, made according to conduit disinfector 200 to harvest the unlimited reflections, has disinfection channel length L=100 cm, diameter D=10 cm. The treated air flow rate is G=100 LPM, and GUV light power is 1.2 W. The doses delivered to the air flow with different impinge angles are plotted in FIG. 12 (following Eq. 8). Selecting practical reflectance R=90% and impinge angle θ=15°, this device delivers about 292 mJ/cm$^2$ to 100 LPM air flow, meaning it can treat air flow of 17,000 LPM to deactivate 99.9% of SARS-Cov-2 viruses.

Figure 13:
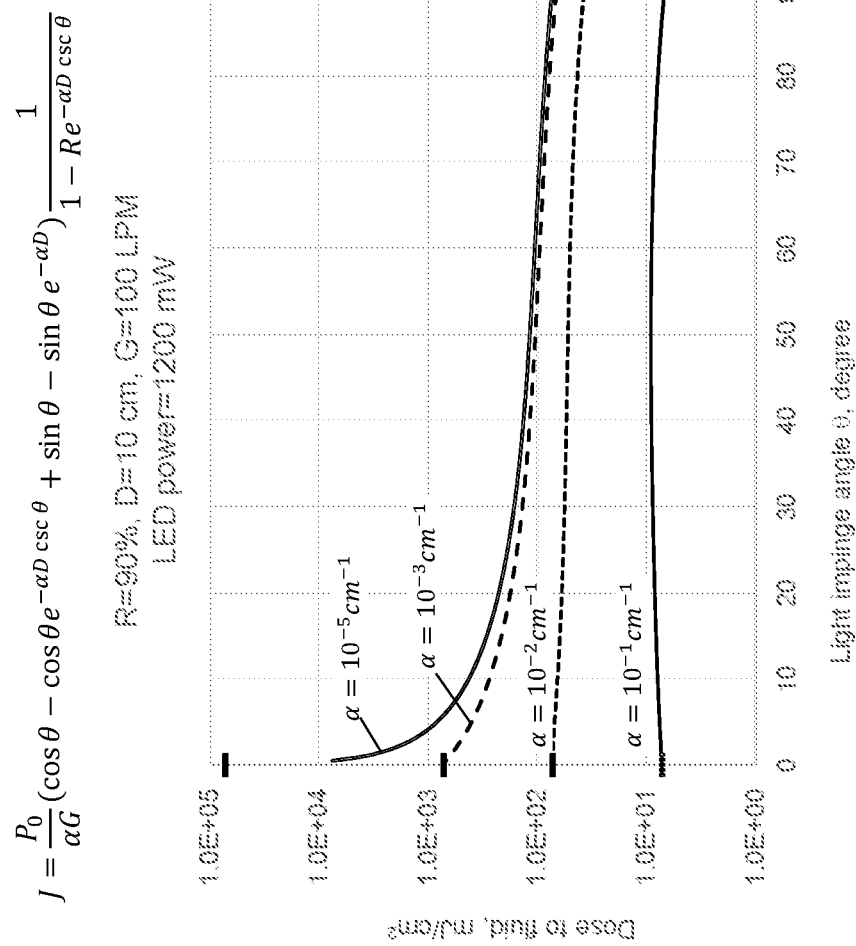
FIG. 13 plots doses as function of light impinge angles for different fluid GUV absorption coefficients for a conduit disinfector according to an embodiment of the present disclosure.

A fluid disinfector, made according to conduit disinfector 200 to harvest the unlimited reflections, has disinfection channel length L=100 cm, diameter D=10 cm. The treated fluid can be air, water, and the like, with absorption coefficient α ranging from $10^{-5}$ to $10^{-1}$ cm$^{-1}$ with flow rate G=100 LPM and GUV light power 1.2 W. The doses delivered to the fluid flow with different impinge angles are plotted in FIG. 13 (following Eq. 6) for a fixed reflectance of 90%. As seen, the less the absorption coefficient, the higher the dose delivered to the fluid. For fluids with large absorption coefficients ($\geq 10^{-1}$ cm$^{-1}$), the dose delivery has weak dependence on light impinge angle. For smaller absorption coefficients, dose delivery is more efficient at small impinge angles (parallel delivery the best). Also, when the impinge angle approaches zero, for mid to large absorption coefficients ($\alpha \geq 10^{-3}$ cm$^{-1}$), doses delivered readily converge with the parallel beam limits (Eq. 2), which are marked as horizontal bars on the y-axis in FIG. 13. Selecting practical reflectance R=90% and impinge angle θ=15°, this device delivers about 62 mJ/cm$^2$ to 100 LPM fluid of absorption coefficient $\alpha = 10^{-2}$ cm$^{-1}$ (clean water). As a reference, class A water disinfection requires GUV dose of 40 mJ/cm$^2$.

Generally, the length L and diameter D of the fluid disinfection channel 221 can be in the range of 10-500 cm and 5-500 cm, respectively, and dose delivered to the fluid can be calculated by Eq. 6. For fluid such as air of negligible DUV absorption coefficient, dose delivered can be calculated using Eq. 8. For example, the air flow rate G can be in the range of 60,000-6,000,000 LPM and GUV light power can be in the range of 1.0-100 W for general disinfection purpose.

Figure 14:
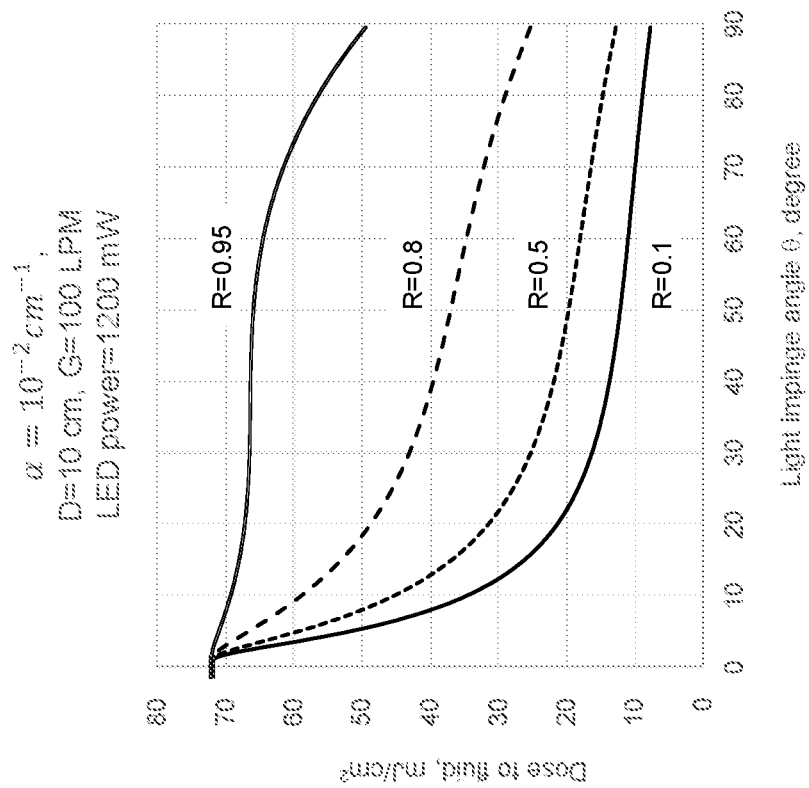
FIG. 14 plots doses as function of light impinge angles for four different reflectance of a conduit disinfector according to an embodiment of the present disclosure.

According to the parallel beam limit (Eq. 2), another aspect of the present disclosure is to provide a parallel beam fluid conduit disinfector, where the disinfection light beams impinge parallel to the flowing fluid (i.e., the impinge angle θ=0°). This embodiment guarantees designed dose delivery regardless of the reflectance of the disinfection channel. For demonstration, still another fluid disinfector, made according to fluid conduit disinfector 100 or 200, has disinfection channel length L=100 cm, diameter D=10 cm. The impact on dose delivery of reflectance of the disinfection channel is investigated and plotted in FIG. 14, where the absorption coefficient is kept constant at $\alpha = 10^{-2}$ cm$^{-1}$ (for clean water). As seen, since a is fixed, regardless of reflectance, at parallel beam limit, all doses delivered converge into a single point according to Eq. 2

$$\left(J = \frac{P_0}{\alpha G}\right),$$

which is 72 mJ/cm$^2$ for the given parameters (G=100 LPM, $P_0$=1200 mW and $\alpha = 10^{-2}$ cm$^{-1}$). Also noticed is that when the reflectance of the disinfection channel is compromised, smaller impinge angle is preferred in order to obtain more dosage delivered to the fluid.

Figure 15:
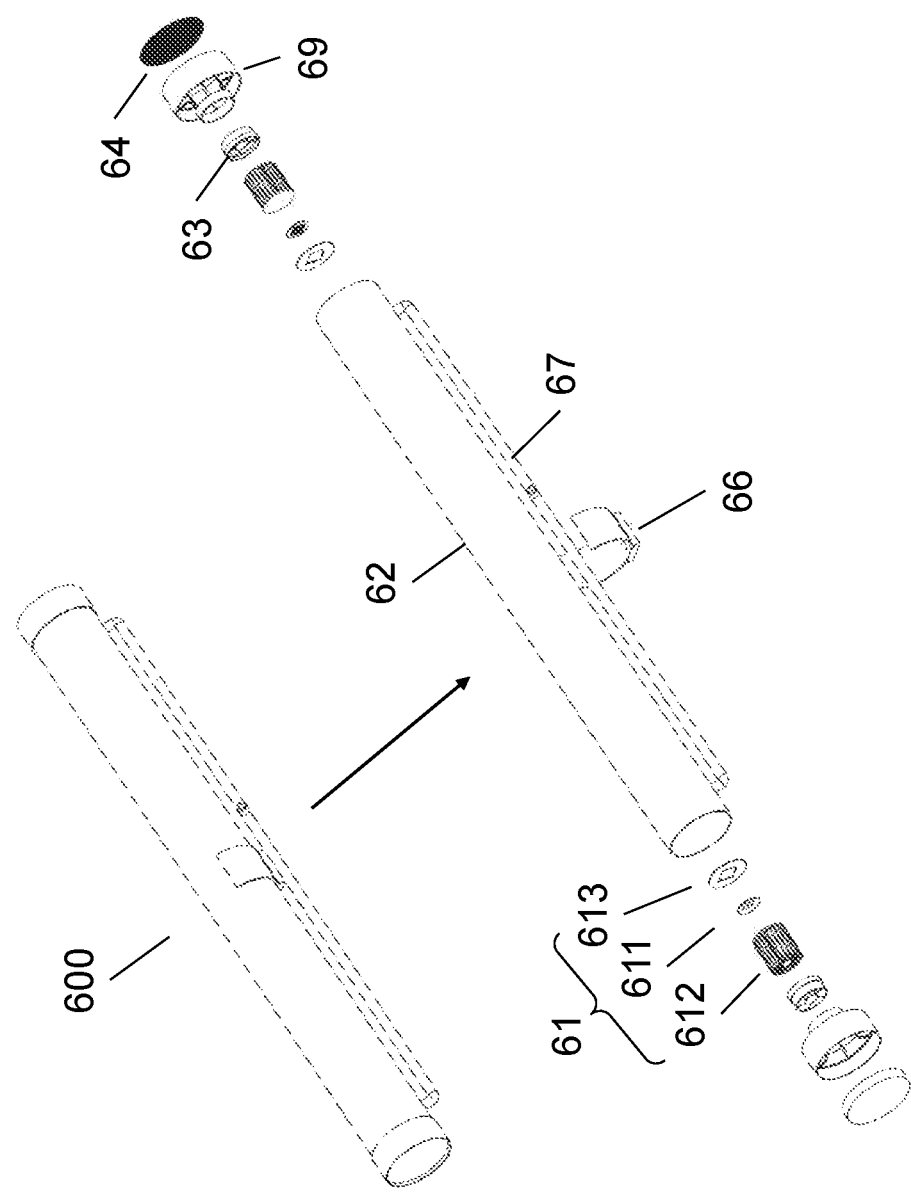
FIG. 15 shows perspective and exploded views of a fluid conduit disinfector according to an embodiment of the present disclosure.

Shown in FIG. 15 are perspective and exploded views of a fluid conduit disinfector 600, made according to fluid conduit disinfector 100. As seen, the main components of fluid conduit disinfector 600 are a cylindrical conduit 62 and two GUV light sources 61, which include a GUV light module 611, a heat sink 612, and a GUV reflective cap 613. The enlarged perspective and exploded views of GUV light source 61 are presented in FIG. 16. As shown, GUV light module 611 can be an array of DUV LEDs. Heat sink 612 is made of metal with fin structure on outer side wall to dissipate heat efficiently for GUV light module 611. Fan 63 is assembled with GUV light source 61, pumping fluid such as air through finned heat sink 612, providing fluid for disinfection as well as cooling heat sink 612. Light module 611 sits on heat sink 612 and is optionally capped with a GUV light reflective cap 613. The surface of GUV reflective cap 613 facing the fluid disinfection channel is GUV light reflective, which can be made from any suitable GUV light reflective material such as described previously in this specification. Therefore, only the light emitting area of light module 611 may be not GUV reflective. Conduit disinfector 600 may further contain a power supply system 67, a mount 66 and a fixture 69. Fixture 69 holds the assembly of GUV light source 61 and fan 63, and a filter 64. The surface of filters 64 and fans 63 can be coated with GUV reflective materials, e.g., coated with aluminum thin film with GUV reflectance of 90%, or coated with teflon with DUV reflectance of 95%, or coated with microporous teflon with reflectance of 98-99%.

Figure 16:
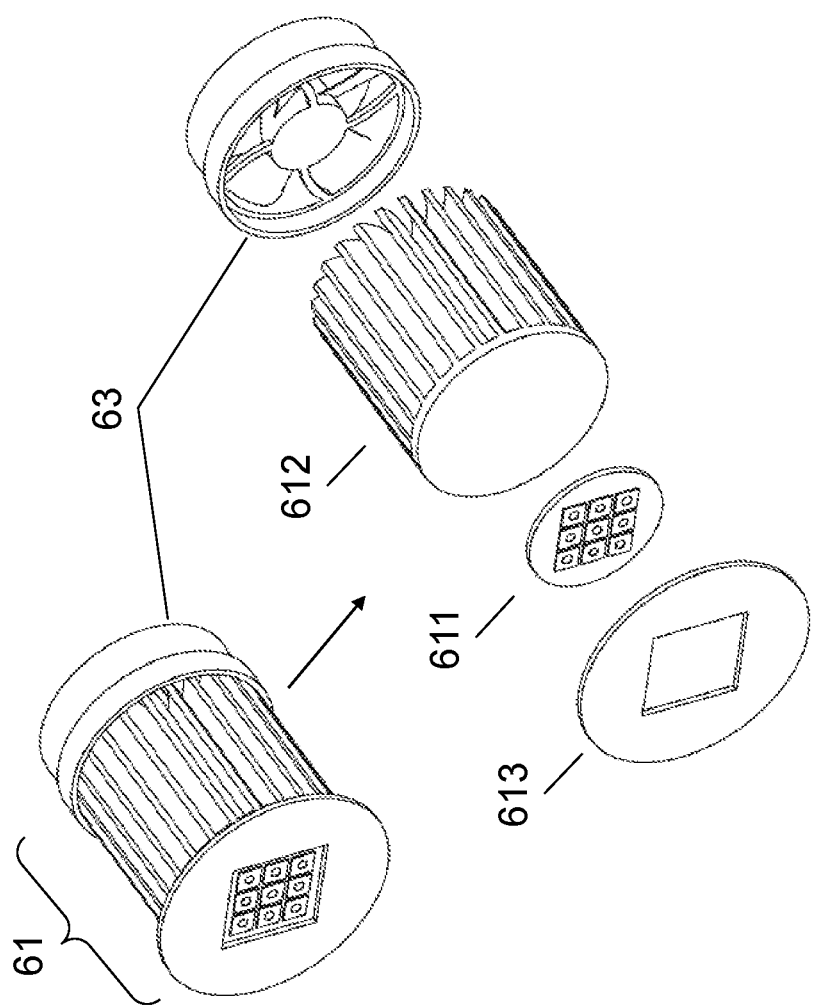
FIG. 16 shows perspective and exploded views of a GUV light source and fan assembly according to an embodiment of the present disclosure.
Figure 17:
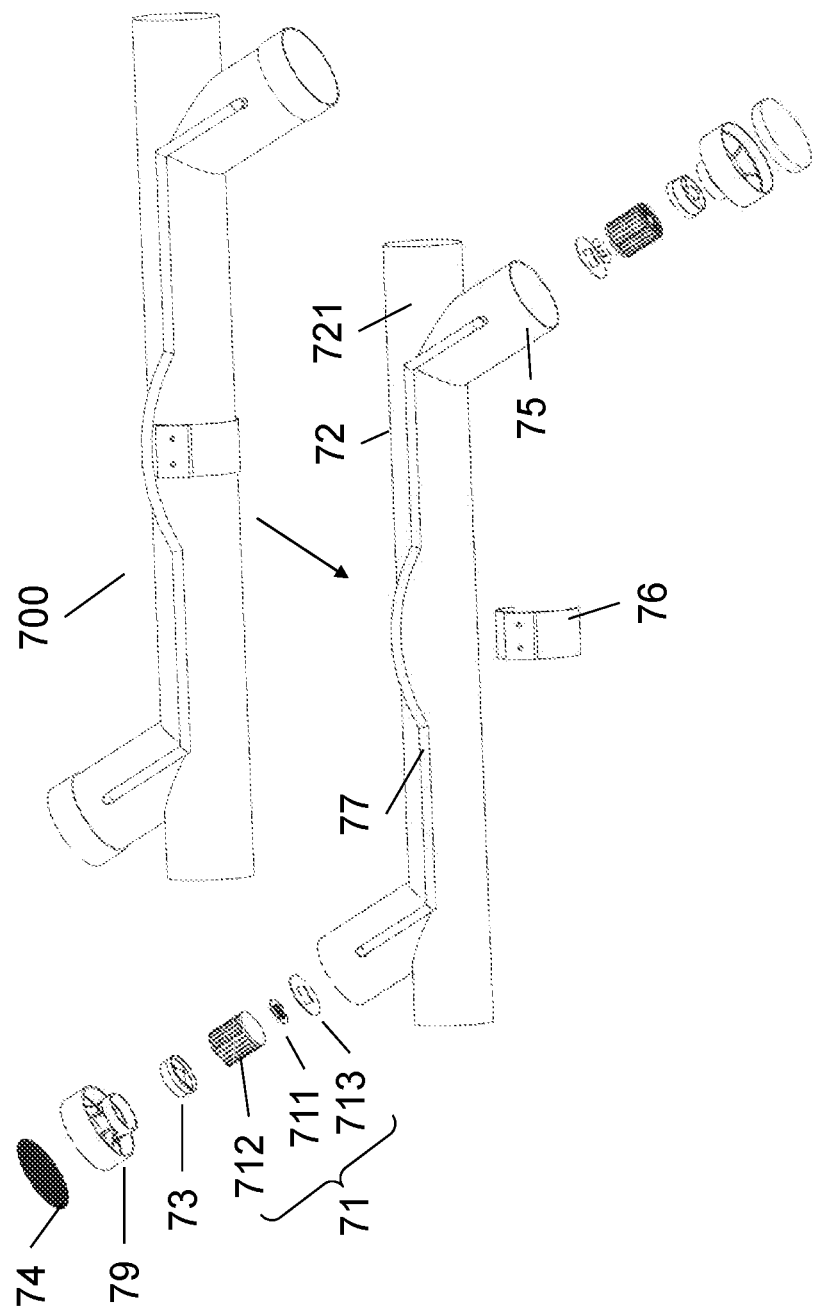
FIG. 17 shows perspective and exploded views of a fluid conduit disinfector according to an embodiment of the present disclosure.

Shown in FIG. 17 are perspective and exploded views of another fluid conduit disinfector 700, made according to fluid conduit disinfectors 200, 400 or 500. GUV light source 71, fan 73 and filter 74 are retrieved away from the fluid disinfection channel, so that light can bounce back and forth within the cylindrical disinfection channel 721 continuously. GUV light source 71, fan 73, filter 74 and fixture 79 are assembled in another cylindrical conduit 75, which joins cylindrical conduit 72 in a slanted angle. The slanted angle, which is the angle between the axis of cylindrical conduit 75 and the axis of cylindrical conduit 72, can be in the range of 30-60°. The perspective and exploded views of GUV light source 71 are similar to GUV light source 61, which is illustrated in FIG. 16.

Figure 19:
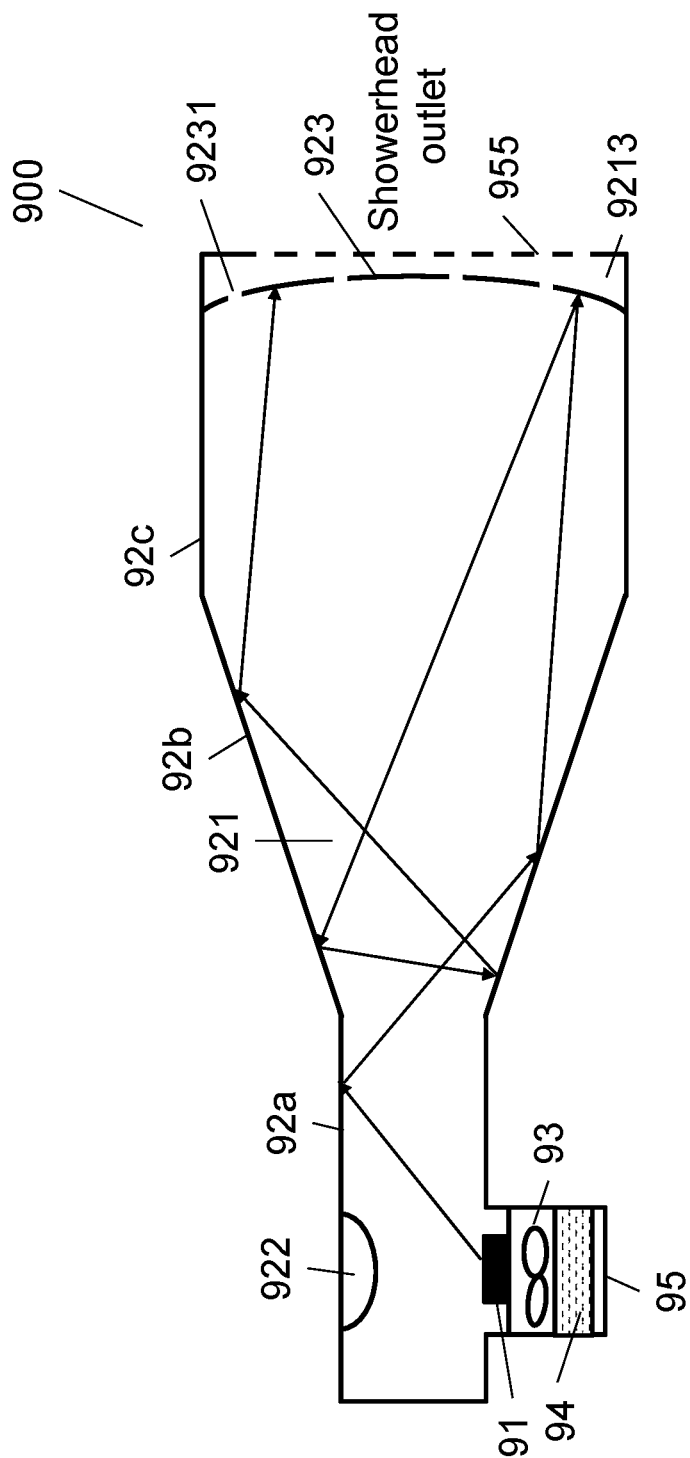
FIG. 19 illustrates a cross-sectional schematic view of a fluid conduit disinfector according to an embodiment of the present disclosure.
Figure 20:
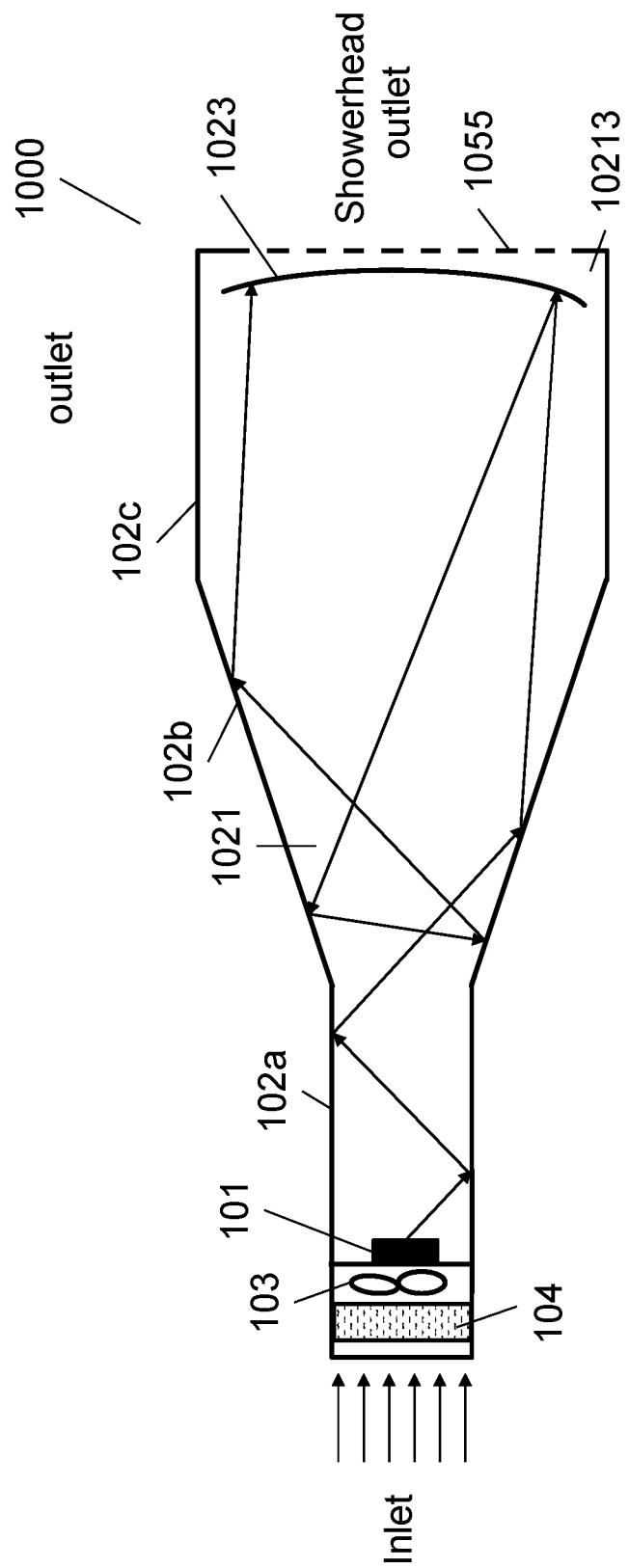
FIG. 20 illustrates a cross-sectional schematic view of a fluid conduit disinfector according to an embodiment of the present disclosure.

According to another aspect of the present disclosure, a fluid conduit disinfector 900 is provided with a cross-sectional schematic view illustrated in FIG. 19, capable of housing unlimited light reflections. It is a modification of conduit disinfector 200, with only one set of GUV light source 91, fan 93 and filter 94, assembled in fluid inlet conduit 95, which joins conduit 92 perpendicularly or at a slanted angle. Optionally, GUV light source 91 emits GUV light upwardly, with a large divergence or aperture angle (e.g., 120°-180°). To further reduce impinge angle θ, a convex reflector 922 can be placed on the inner surface of conduit 92, facing directly to GUV light source 91 across the disinfection channel 921. The most significant difference between conduit disinfectors 200 and 900 is that in conduit disinfector 900, conduit 92 contains three parts, namely conduits 92a, 92b, and 92c. Conduit 92a, closer to GUV light source 91, has smaller, optionally significantly smaller diameter than that of conduit 92c, which is further away from GUV light source 91. For example, for cylindrical shaped conduits 92a and 92c, the diameter of conduit 92a can be 10-30% of that of conduit 92c. Conduit 92b, with gradually increasing diameter, connecting conduits 92a and 92C. The gradient of the diameter of conduit 92b is designed to reduce the probability of light beams being reflected back to conduit 92a, therefore, it can be gradual, or abrupt (meaning conduit 92b vanishes). Conduits 92a, 92b and 92c collectively enclose a disinfection channel 921. This arrangement makes light beams significantly less likely to bounce back to GUV light source 91. The end of conduit 92c is provided with a showerhead 955 for disinfected air to exit uniformly. There is a reflector 923 in front of showerhead 955, to reflect light and confine light within disinfection channel 921. Reflector 923 can be planar, parabolic, spherical, or aspheric. A space 9213 between reflector 923 and showerhead 955 is in fluid connection to disinfection channel 921 (e.g., via through holes 9231 in reflector 923 as illustrated in FIG. 19), buffering disinfected air prior to exit. Reflector 923 can cover the entire cross section of disinfection channel 921 with through holes 9231 formed thereon to allow the fluid to pass through, or reflector 923 only cover a central part of the cross section of disinfection channel 921 with a gap formed between the edge of reflector 923 and the inner side wall of disinfection channel 921 as shown in FIG. 20, and in this case no need to form through holes 9231. The surface of reflector 923 facing disinfection channel 921 can be made of any suitable GUV light reflective material such as those described previously in this specification. The length and diameter of conduit 92a can be in the range of 10-100 cm and 5-20 cm, respectively. The length and diameter of conduit 92c can be in the range of 10-100 cm and 20-200 cm, respectively. The length of conduit 92b can be in the range of 0-30 cm. Further, even though conduit 92c can be of cylindrical shape, it can be of other shapes as well, such as rectangular or spherical shapes. Conduit 92a also can be of cylindrical or other shapes such as rectangular or spherical shapes.

According to still another aspect of the present disclosure, a fluid conduit disinfector 1000 is provided with a cross-sectional schematic view illustrated in FIG. 20, capable of housing unlimited light reflections. Conduit disinfector 1000 is a modification of conduit disinfector 900, with a set of GUV light source 101, fan 103 and filter 104 assembled in conduit 102a. Conduit 102 contains three parts, namely conduits 102a, 102b, and 102c. Conduit 102a, also housing GUV light source 101, has smaller, optionally significantly smaller diameter than that of conduit 102c, which is further away from GUV light source 101. For example, for cylindrical shaped conduits 102a and 102c, the diameter of conduit 102a can be 10-30% of that of conduit 102c. Conduit 102b, with gradually increasing diameter, connecting conduits 102a and 102C. The gradient of the diameter of conduit 102b is designed to reduce the probability of light beams being reflected back to conduit 102a, therefore, it can be gradual, or abrupt (meaning conduit 102b vanishes). Conduits 102a, 102b and 102c collectively enclose a disinfection channel 1021. This arrangement makes light beams significantly less likely to bounce back to GUV light source 101. The end of conduit 102c is made into a showerhead 1055 for disinfected air to exit uniformly. There is a reflector 1023 in front of showerhead 1055, to reflect light and confine light within disinfection channel 1021. Reflector 1023 can be planar, parabolic, spherical, or aspheric. A space 10213, between reflector 1023 and showerhead 1055, is in fluid connection to disinfection channel 1021, buffering disinfected air prior to exit. Reflector 1023 can cover the entire cross section of disinfection channel 1021 with through holes formed thereon to allow the fluid to pass through, or reflector 1023 only cover a central part of the cross section of disinfection channel 1021 with a gap formed between the edge of reflector 1023 and the inner side wall of disinfection channel 1021. The surface of reflector 1023 facing disinfection channel 1021 can be made of any suitable GUV light reflective material such as those described previously in this specification. The length and diameter of conduit 102a can be in the range of 10-100 cm and 5-20 cm, respectively. The length and diameter of conduit 102c can be in the range of 10-100 cm and 20-200 cm, respectively. The length of conduit 102b can be in the range of 0-30 cm. Further, even though conduit 102c can be of cylindrical shape, it can be of other shapes as well, such as rectangular or spherical shapes. Conduit 102a also can be of cylindrical or other shapes such as rectangular or spherical shapes.

Figure 21:
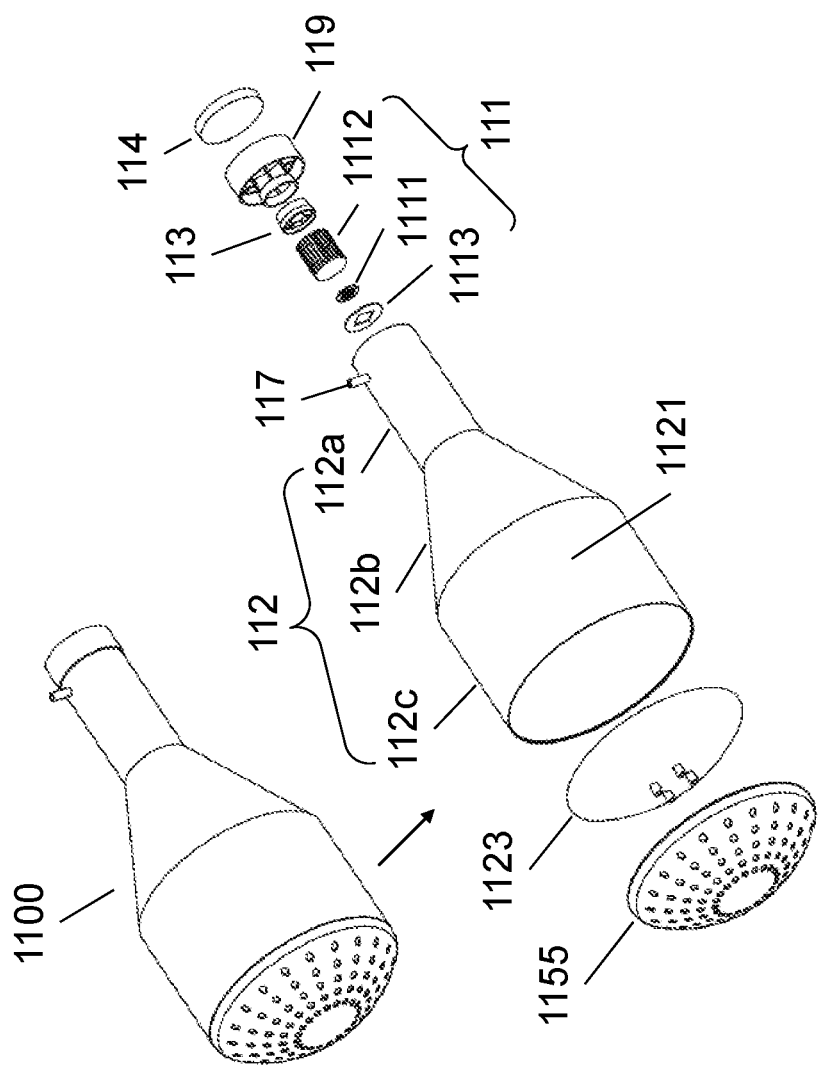
FIG. 21 shows perspective and exploded views of a fluid conduit disinfector according to an embodiment of the present disclosure.

Shown in FIG. 21 are perspective and exploded views of a fluid conduit disinfector 1100, made according to conduit disinfector 1000. As seen, the main components of conduit disinfector 1100 are a conduit 112 (including conduits 112a, 112b and 112c) and one GUV light sources 111, which are made of a GUV light module 1111, a heat sink 1112, and a GUV reflective cap 1113. The perspective and exploded view of GUV light source 111 are similar to GUV light source 61, which is illustrated in FIG. 16. Conduit disinfector 1100 further has a power supply system 117 and a fixture 119. Fixture 119 holds the assembly of GUV light source 111 and fan 113, and a filter 114.

Figure 22:
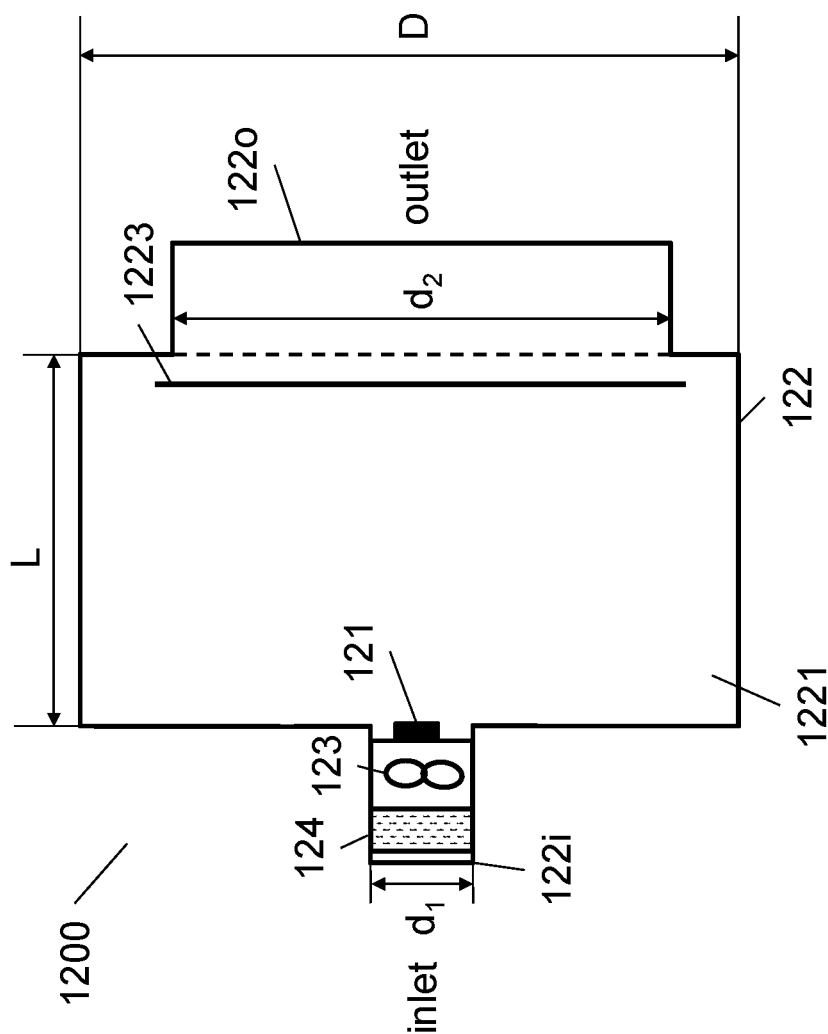
FIG. 22 illustrates a cross-sectional schematic view of a fluid conduit disinfector according to an embodiment of the present disclosure.

Further, for fluid conduit disinfectors with fluids of negligible GUV light absorption coefficient and capable of housing unlimited light reflections, it is noticed from Eqs. 7 and 8 that the dose delivered to the fluid is proportional to the conduit lateral dimension (or diameter) D. Therefore, a conduit disinfector of large lateral dimension is preferred. A cross-sectional illustration of a fluid conduit disinfector 1200 is shown in FIG. 22 according to this aspect of the present disclosure. As seen, the main components of conduit disinfector 1200 are a conduit 122 and one GUV light sources 121, which can be made of a GUV light module, a heat sink, and a GUV reflective cap, similar to GUV light source 61. There is a reflector 1223 in front of fluid outlet 122o, to reflect light and confine light within disinfection channel 1221. Reflector 1223 can be of planar, parabolic, spherical, or aspheric shape. Fluid flows into disinfection channel 1221 from the inlet 122i through filter 124 sucked by fan 123, and disinfected fluid is discharged from the outlet 122o, which can contain a showerhead structure. Reflector 1223 is positioned in front of the outlet 122o and covers the entire cross section of the outlet 122o. There is a gap between reflector 1223 and the inner end surface of disinfection channel 1221 for the fluid to flow out therethrough as shown in FIG. 22. In other embodiments, reflector 1223 may not cover the entire cross section of the outlet 122o and through holes can be formed in reflector 1223 for the fluid to flow through. The outstanding feature of conduit disinfector 1200 is that its lateral dimension or diameter D is significantly larger than the lateral dimension $d_1$ of the inlet 122i, and is optionally larger than the length L of the disinfection channel 1221. For example, $$\frac{D}{d_1} \geq 5, \text{ and } \frac{D}{L} \geq 3.$$

The lateral dimension or diameter $d_2$ of the outlet 122o can be about 50%-95% of the lateral dimension or diameter of conduit disinfector 1200, D, so that disinfected air is uniformly discharged from the outlet 122o with small velocity. The requirement of D to be significantly larger than $d_1$ is to ensure unlimited light reflections within disinfection channel 1221. The requirement of D to be larger than L is to save space for conduit disinfector 1200. In one embodiment, $d_1$=10 cm, D=100 cm, L=20 cm, when GUV light source 121 shines DUV light of power 2.5 W with impinge angles ≤30°, and if the disinfection channel 1221 is of DUV light reflectance R=90%, the delivered GUV dose will be larger than 45 mJ/cm² to clean air flow of 7500 LPM, according to eq. 8. This dose is sufficient to thoroughly disinfect the air in a 75 m³ room in 10 minutes.

The present disclosure has been described using exemplary embodiments. However, it is to be understood that the scope of the present disclosure is not limited to the disclosed embodiments. On the contrary, it is intended to cover various modifications and similar arrangement or equivalents which can be obtained by a person skilled in the art without creative work or undue experimentation. The scope of the claims, therefore, should be accorded the broadest interpretation so as to encompass all such modifications and similar arrangements and equivalents.

What is claimed is:

1. A fluid conduit disinfector comprising:
a conduit with a fluid disinfection channel defined by inner side surface of the conduit, wherein the inner side surface of the conduit is reflective with a germicidal ultraviolet (GUV) light reflectance R of 50%-99%, the fluid disinfection channel with a length L and a lateral dimension D has an inlet for receiving a fluid to be disinfected and an outlet for the fluid to be disinfected to exit after being disinfected;
a GUV light source disposed at the inlet, or the outlet, or both the inlet and the outlet within the fluid disinfection channel for emitting GUV light into the fluid disinfection channel at a light impinge angle θ along an axial direction of the fluid disinfection channel, wherein $$\theta \geq \tan^{-1}\frac{D}{L}[\log_R(1-\rho)-1],$$

ρ is a design efficiency and $\rho=1-R^{n+1}$, n is reflection times of the GUV light within the fluid disinfection channel and $$n = \frac{1}{D \cot \theta};$$

a fan for forcing a fluid to be disinfected to flow through the fluid disinfection channel, and a filter for filtering particles from the fluid.

2. The fluid conduit disinfector of claim 1, further comprising a reflector disposed within the conduit at the inlet, or the outlet, or both the inlet and the outlet of the fluid disinfection channel, wherein the reflector has an inclined reflecting surface facing and surrounding the GUV light source.

3. The fluid conduit disinfector of claim 1, wherein the inner side surface of the conduit is made of polished aluminum or coated with aluminum film with a GUV reflectance of 80-90%, or coated with teflon with a GUV reflectance of 90-95%, or coated with microporous teflon with a GUV reflectance of 95-99%.

4. The fluid conduit disinfector of claim 1, wherein the fluid disinfection channel is of a cylindrical shape, the GUV light source comprises a heat sink, a GUV light module having an array of GUV LEDs, and a GUV reflective cap.

5. The fluid conduit disinfector of claim 1, wherein the fluid disinfection channel is of a Z-shape.

6. The fluid conduit disinfector of claim 1, wherein the fan and the filter are GUV light reflective.

7. A fluid conduit disinfector comprising:

a conduit with a fluid disinfection channel defined by inner side surface of the conduit, wherein the inner side surface of the conduit is reflective with a germicidal ultraviolet (GUV) light reflectance R of 50%-99%, the fluid disinfection channel has an inlet at a first end for receiving a fluid to be disinfected and an outlet at a second end for the fluid to be disinfected to exit after being disinfected;

a GUV light source disposed at the inlet, or the outlet, or both the inlet and the outlet within the fluid disinfection channel for emitting GUV light into the fluid disinfection channel along an axial direction of the fluid disinfection channel;

a fan for forcing a fluid to be disinfected to flow through the fluid disinfection channel, and a filter for filtering particles from the fluid;

wherein the GUV light source emits GUV light in the form of a light cone with a cone angle $2\beta$ with a central axis of the light cone being aligned with a central axis of the fluid disinfection channel, and satisfies the following inequality:

$$\beta \geq \tan^{-1} D/L [\log_R(1-\rho) - 1]$$

where L is a length of the fluid disinfection channel, D is a lateral dimension of the fluid disinfection channel, $2\beta$ is the cone angle of a light cone which consists at least 50% of total optical power emitted by the GUV light source, and $\rho$ is design efficiency of the fluid conduit disinfector and selected to be in the range of 0.8-0.99, $\rho = 1 - R^{n+1}$, and n is light reflection times within the fluid disinfection channel.

8. The fluid conduit disinfector of claim 7, wherein the fluid disinfection channel is of a cylindrical shape, and the GUV light source comprises a heat sink, a GUV light module having an array of GUV LEDs, and a GUV reflective cap.

9. The fluid conduit disinfector of claim 8, further comprising a reflector disposed within the conduit at the inlet, or outlet, or both the inlet and the outlet of the fluid disinfection channel, wherein the reflector has an inclined reflecting surface facing and surrounding the GUV light source.

10. The fluid conduit disinfector of claim 7, wherein the inner side surface of the conduit is made of polished aluminum or coated with aluminum film with a GUV reflectance of 80-90%, or coated with teflon with a GUV reflectance of 90-95%, or coated with microporous teflon with a GUV reflectance of 95-99%.

* * * * *